(12) United States Patent
Schaller et al.

(10) Patent No.: US 8,470,043 B2
(45) Date of Patent: Jun. 25, 2013

(54) TISSUE REMOVAL TOOLS AND METHODS OF USE

(75) Inventors: Laurent B. Schaller, Los Altos, CA (US); Steven S. Golden, Menlo Park, CA (US); Jeffrey L. Emery, Emerald Hills, CA (US); James K. Lee, San Mateo, CA (US); Mark Y. Hirotsuka, San Jose, CA (US); Russell J. Borg, Campbell, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 666 days.

(21) Appl. No.: 12/640,171

(22) Filed: Dec. 17, 2009

(65) Prior Publication Data

US 2010/0161060 A1    Jun. 24, 2010

Related U.S. Application Data

(60) Provisional application No. 61/140,401, filed on Dec. 23, 2008.

(51) Int. Cl.
*A61F 2/44* (2006.01)

(52) U.S. Cl.
USPC ........................................ 623/17.16

(58) Field of Classification Search
USPC ............... 606/86 R, 113, 114, 159, 167, 169, 606/170–172, 177–183
See application file for complete search history.

(56) References Cited

U.S. PATENT DOCUMENTS

| | | | |
|---|---|---|---|
| 3,807,390 A | 4/1974 | Ostrowski et al. |
| 4,846,175 A | 7/1989 | Frimberger |
| 5,129,889 A | 7/1992 | Hahn et al. |
| 5,219,358 A | 6/1993 | Bendel et al. |
| 5,267,994 A | 12/1993 | Gentelia et al. |
| 5,342,394 A | 8/1994 | Matsuno et al. |
| 5,345,945 A | 9/1994 | Hodgson et al. |
| 5,366,490 A | 11/1994 | Edwards et al. |
| 5,383,884 A | 1/1995 | Summers |
| 5,397,304 A | 3/1995 | Truckai |
| 5,423,806 A | 6/1995 | Dale et al. |
| 5,433,739 A | 7/1995 | Sluijter et al. |
| 5,487,757 A | 1/1996 | Truckai et al. |
| 5,500,012 A | 3/1996 | Brucker et al. |
| 5,571,147 A | 11/1996 | Sluijter et al. |
| 5,599,346 A | 2/1997 | Edwards et al. |
| 5,697,909 A | 12/1997 | Eggers et al. |
| 5,755,732 A | 5/1998 | Green et al. |
| 5,788,713 A | 8/1998 | Dubach et al. |
| 5,871,501 A | 2/1999 | Leschinsky et al. |
| 5,885,217 A | 3/1999 | Gisselberg et al. |

(Continued)

FOREIGN PATENT DOCUMENTS

| | | |
|---|---|---|
| DE | 4222121 C1 | 9/1993 |
| EP | 0682910 A1 | 11/1995 |
| WO | WO98/17190 A3 | 4/1998 |

*Primary Examiner* — Eduardo C Robert
*Assistant Examiner* — Tara Carter
(74) *Attorney, Agent, or Firm* — Cook Alex Ltd.

(57) ABSTRACT

Discectomy or disc preparation system that includes a guide member that is changeable from a deployment configuration for insertion into an intervertebral disc space to a deployed configuration upon being deployed into the intervertebral disc. The system also includes at least one tissue manipulator, such as cutting, scraping and extraction elements, that can be moved or tracked longitudinally along the guide member into and through the intervertebral disc space.

23 Claims, 10 Drawing Sheets

U.S. PATENT DOCUMENTS

| | | |
|---|---|---|
| 5,916,166 A | 6/1999 | Reiss et al. |
| 5,980,471 A | 11/1999 | Jafari |
| 5,980,504 A * | 11/1999 | Sharkey et al. ............... 604/510 |
| 6,007,570 A | 12/1999 | Sharkey et al. |
| 6,099,514 A | 8/2000 | Sharkey et al. |
| 6,126,682 A | 10/2000 | Sharkey et al. |
| 6,224,630 B1 | 5/2001 | Bao et al. |
| 6,245,107 B1 | 6/2001 | Ferree |
| 6,277,112 B1 | 8/2001 | Underwood et al. |
| 6,375,635 B1 | 4/2002 | Moutafis et al. |
| 6,387,130 B1 | 5/2002 | Stone et al. |
| 6,419,704 B1 | 7/2002 | Ferree |
| 6,468,270 B1 | 10/2002 | Hovda et al. |
| 6,488,710 B2 | 12/2002 | Besselink |
| 6,491,690 B1 | 12/2002 | Goble et al. |
| 6,530,926 B1 | 3/2003 | Davison |
| 6,551,319 B2 | 4/2003 | Lieberman |
| 6,558,386 B1 | 5/2003 | Cragg |
| 6,558,390 B2 | 5/2003 | Cragg |
| 6,562,033 B2 | 5/2003 | Shah et al. |
| 6,592,625 B2 | 7/2003 | Cauthen |
| 6,607,530 B1 | 8/2003 | Carl et al. |
| 6,676,665 B2 | 1/2004 | Foley et al. |
| 6,714,822 B2 | 3/2004 | King et al. |
| 6,726,684 B1 | 4/2004 | Woloszko et al. |
| 6,749,605 B2 | 6/2004 | Ashley et al. |
| 6,764,491 B2 | 7/2004 | Frey et al. |
| 6,767,347 B2 | 7/2004 | Sharkey et al. |
| 6,821,276 B2 | 11/2004 | Lambrecht et al. |
| 6,830,570 B1 | 12/2004 | Frey et al. |
| 6,878,155 B2 | 4/2005 | Sharkey et al. |
| 6,923,811 B1 | 8/2005 | Carl et al. |
| 6,939,351 B2 | 9/2005 | Eckman |
| 6,953,458 B2 | 10/2005 | Loeb |
| 6,964,667 B2 | 11/2005 | Shaolian et al. |
| 6,976,949 B2 | 12/2005 | Winkler et al. |
| 7,004,970 B2 | 2/2006 | Cauthen, III et al. |
| 7,025,765 B2 | 4/2006 | Balbierz et al. |
| 7,052,516 B2 | 5/2006 | Cauthen, III et al. |
| 7,056,321 B2 | 6/2006 | Pagliuca et al. |
| 7,069,087 B2 | 6/2006 | Sharkey et al. |
| 7,114,501 B2 | 10/2006 | Johnson et al. |
| 7,124,761 B2 | 10/2006 | Lambrecht et al. |
| 7,144,397 B2 | 12/2006 | Lambrecht et al. |
| 7,179,225 B2 | 2/2007 | Shluzas et al. |
| 7,211,055 B2 | 5/2007 | Diederich et al. |
| 7,241,297 B2 | 7/2007 | Shaolian et al. |
| 7,282,020 B2 | 10/2007 | Kaplan |
| 7,309,336 B2 | 12/2007 | Ashley et al. |
| 7,318,823 B2 | 1/2008 | Sharps et al. |
| 7,318,826 B2 | 1/2008 | Teitelbaum et al. |
| 7,322,962 B2 | 1/2008 | Forrest |
| 7,331,956 B2 | 2/2008 | Hovda et al. |
| 7,331,963 B2 | 2/2008 | Bryan et al. |
| RE40,156 E | 3/2008 | Sharps et al. |
| 2001/0031981 A1* | 10/2001 | Evans et al. ................... 606/200 |
| 2002/0026197 A1 | 2/2002 | Foley et al. |
| 2002/0147444 A1* | 10/2002 | Shah et al. ...................... 606/28 |
| 2002/0156530 A1 | 10/2002 | Lambrecht et al. |
| 2003/0014047 A1 | 1/2003 | Woloszko et al. |
| 2003/0040796 A1 | 2/2003 | Ferree |
| 2003/0158545 A1 | 8/2003 | Hovda et al. |
| 2003/0204189 A1 | 10/2003 | Cragg |
| 2004/0015218 A1 | 1/2004 | Finch et al. |
| 2004/0024463 A1 | 2/2004 | Thomas, Jr. et al. |
| 2004/0049180 A1 | 3/2004 | Sharps et al. |
| 2004/0059333 A1 | 3/2004 | Carl et al. |
| 2004/0073216 A1 | 4/2004 | Lieberman |
| 2004/0092988 A1 | 5/2004 | Shaolian et al. |
| 2004/0106940 A1 | 6/2004 | Shaolian et al. |
| 2004/0116922 A1 | 6/2004 | Hovda et al. |
| 2004/0127893 A1 | 7/2004 | Hovda |
| 2004/0148028 A1 | 7/2004 | Ferree et al. |
| 2004/0153064 A1 | 8/2004 | Foley et al. |
| 2004/0167625 A1 | 8/2004 | Beyar et al. |
| 2004/0260305 A1 | 12/2004 | Gorensek et al. |
| 2005/0021030 A1 | 1/2005 | Pagliuca et al. |
| 2005/0033292 A1 | 2/2005 | Teitelbaum et al. |
| 2005/0049623 A1 | 3/2005 | Moore et al. |
| 2005/0090833 A1 | 4/2005 | DiPoto |
| 2005/0090899 A1 | 4/2005 | DiPoto |
| 2005/0113832 A1 | 5/2005 | Molz, IV et al. |
| 2005/0131540 A1 | 6/2005 | Trieu |
| 2005/0131541 A1 | 6/2005 | Trieu |
| 2005/0137601 A1 | 6/2005 | Assell et al. |
| 2005/0137605 A1 | 6/2005 | Assell et al. |
| 2005/0149049 A1 | 7/2005 | Assell et al. |
| 2005/0187537 A1 | 8/2005 | Loeb et al. |
| 2005/0203527 A1 | 9/2005 | Carrison et al. |
| 2005/0261684 A1 | 11/2005 | Shaolian et al. |
| 2005/0261692 A1 | 11/2005 | Carrison et al. |
| 2006/0015131 A1 | 1/2006 | Kierce et al. |
| 2006/0025797 A1 | 2/2006 | Lock et al. |
| 2006/0036241 A1 | 2/2006 | Siegal |
| 2006/0041295 A1 | 2/2006 | Osypka |
| 2006/0047178 A1 | 3/2006 | Winkler et al. |
| 2006/0058826 A1 | 3/2006 | Evans et al. |
| 2006/0074425 A1 | 4/2006 | Sutterlin et al. |
| 2006/0149268 A1 | 7/2006 | Truckai et al. |
| 2006/0161162 A1 | 7/2006 | Lambrecht et al. |
| 2006/0178666 A1 | 8/2006 | Cosman et al. |
| 2006/0195091 A1 | 8/2006 | McGraw et al. |
| 2006/0195094 A1 | 8/2006 | McGraw et al. |
| 2006/0206116 A1 | 9/2006 | Yeung |
| 2006/0217811 A1 | 9/2006 | Lambrecht et al. |
| 2006/0224154 A1 | 10/2006 | Shadduck et al. |
| 2006/0229625 A1 | 10/2006 | Truckai et al. |
| 2006/0235418 A1 | 10/2006 | Gil et al. |
| 2006/0241577 A1 | 10/2006 | Balbierz et al. |
| 2006/0247600 A1 | 11/2006 | Yeung et al. |
| 2006/0247784 A1 | 11/2006 | Kim |
| 2006/0265076 A1 | 11/2006 | Carter et al. |
| 2006/0287726 A1 | 12/2006 | Segal et al. |
| 2006/0287727 A1 | 12/2006 | Segal et al. |
| 2006/0287730 A1 | 12/2006 | Segal et al. |
| 2007/0016273 A1 | 1/2007 | Scarborough et al. |
| 2007/0027545 A1 | 2/2007 | Carls et al. |
| 2007/0055259 A1 | 3/2007 | Norton et al. |
| 2007/0060935 A1 | 3/2007 | Schwardt et al. |
| 2007/0067035 A1 | 3/2007 | Falahee |
| 2007/0093822 A1 | 4/2007 | Dutoit et al. |
| 2007/0093899 A1 | 4/2007 | Dutoit et al. |
| 2007/0118219 A1 | 5/2007 | Hyde, Jr. |
| 2007/0123888 A1 | 5/2007 | Bleich et al. |
| 2007/0123986 A1 | 5/2007 | Schaller |
| 2007/0149990 A1 | 6/2007 | Palmer et al. |
| 2007/0162032 A1 | 7/2007 | Johnson et al. |
| 2007/0162062 A1 | 7/2007 | Norton et al. |
| 2007/0162127 A1 | 7/2007 | Peterman et al. |
| 2007/0162135 A1 | 7/2007 | Segal et al. |
| 2007/0168041 A1 | 7/2007 | Kadiyala |
| 2007/0168043 A1 | 7/2007 | Ferree |
| 2007/0198021 A1 | 8/2007 | Wales |
| 2007/0198025 A1 | 8/2007 | Trieu et al. |
| 2007/0208426 A1 | 9/2007 | Trieu |
| 2007/0213704 A1 | 9/2007 | Truckai et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0255286 A1 | 11/2007 | Trieu |
| 2007/0255406 A1 | 11/2007 | Trieu |
| 2007/0255703 A1 | 11/2007 | Maruyama et al. |
| 2007/0260252 A1 | 11/2007 | Schmitz et al. |
| 2007/0260270 A1 | 11/2007 | Assell et al. |
| 2007/0260279 A1 | 11/2007 | Hotter et al. |
| 2007/0265652 A1 | 11/2007 | Assell et al. |
| 2007/0265691 A1 | 11/2007 | Swanson |
| 2007/0299521 A1 | 12/2007 | Glenn et al. |
| 2008/0009826 A1 | 1/2008 | Miller et al. |
| 2008/0009828 A1 | 1/2008 | Miller et al. |
| 2008/0009847 A1 | 1/2008 | Ricart et al. |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |

| | | | | | | |
|---|---|---|---|---|---|---|
| 2008/0021435 A1 | 1/2008 | Miller et al. | | 2008/0065093 A1 | 3/2008 | Assell et al. |
| 2008/0027407 A1 | 1/2008 | Miller et al. | | 2008/0065094 A1 | 3/2008 | Assell et al. |
| 2008/0033465 A1 | 2/2008 | Schmitz et al. | | 2008/0086157 A1 | 4/2008 | Stad et al. |
| 2008/0058707 A1 | 3/2008 | Ashley et al. | | | | |
| 2008/0065080 A1 | 3/2008 | Assell et al. | | | | |
| 2008/0065092 A1 | 3/2008 | Assell et al. | | | | |

* cited by examiner

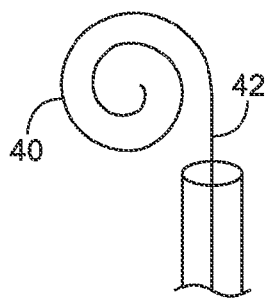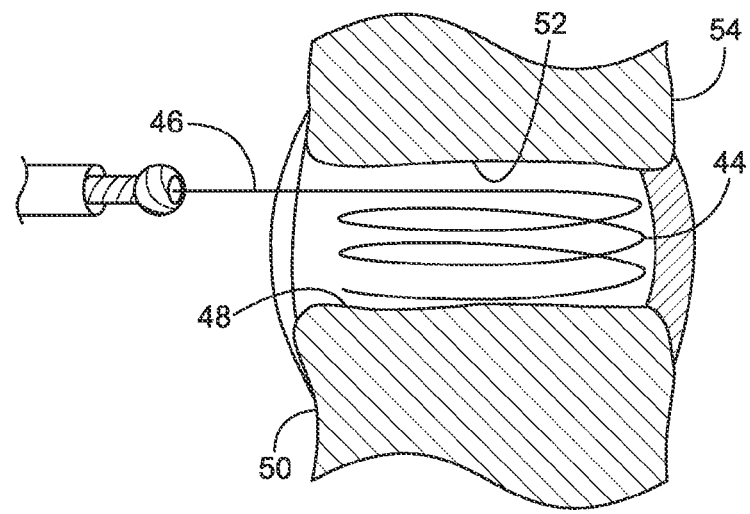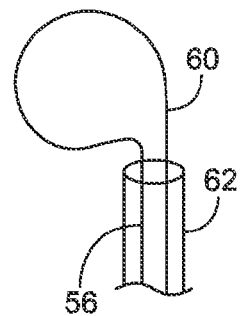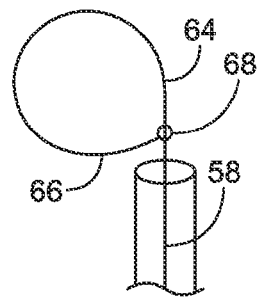
FIG. 7    FIG. 8
FIG. 9    FIG. 10

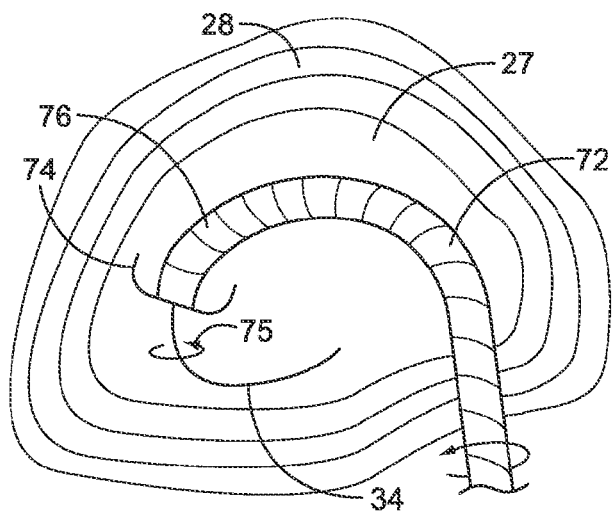
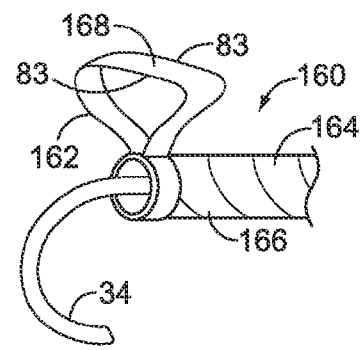
FIG. 26    FIG. 27
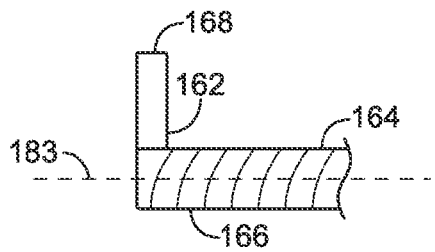
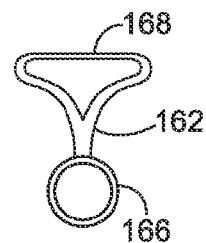
FIG. 28    FIG. 29
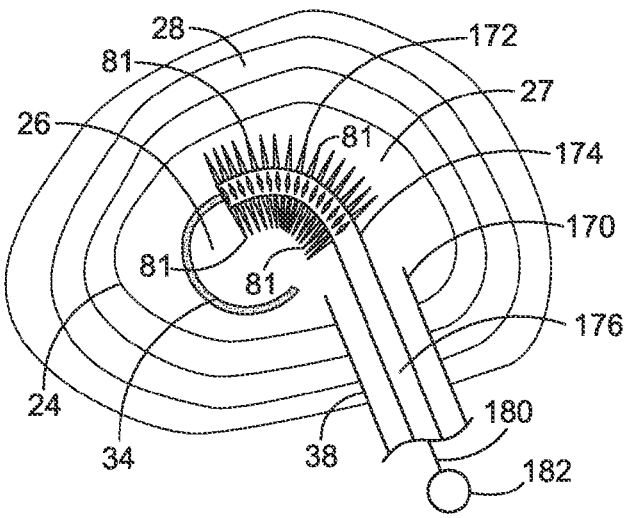
FIG. 30

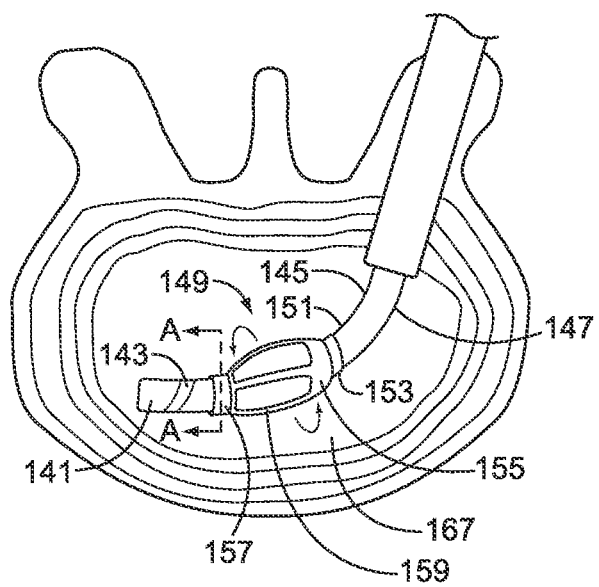
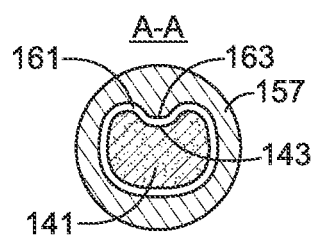
FIG. 35
FIG. 36
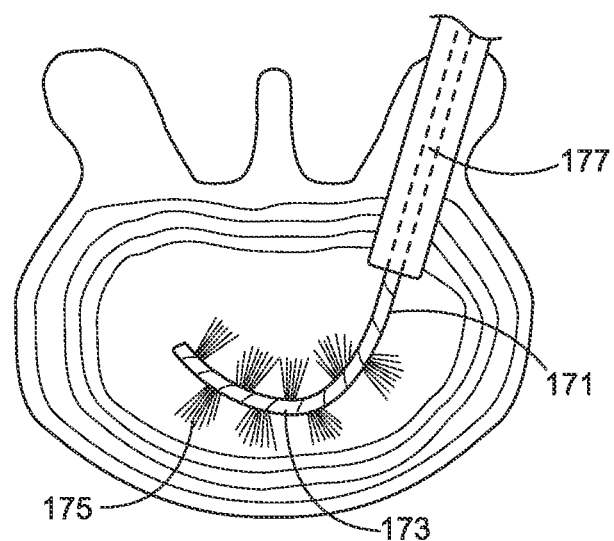
FIG. 37

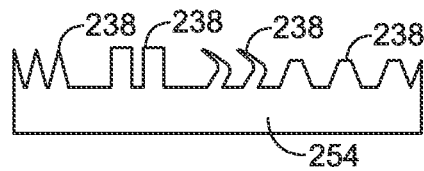
FIG. 52
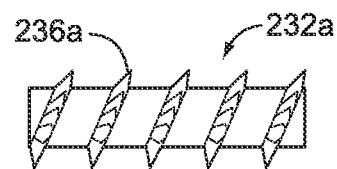
FIG. 53
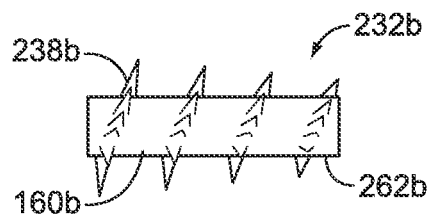
FIG. 54
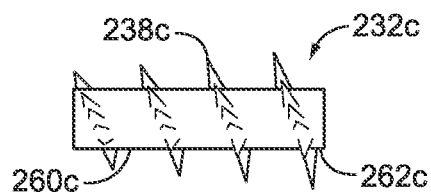
FIG. 55
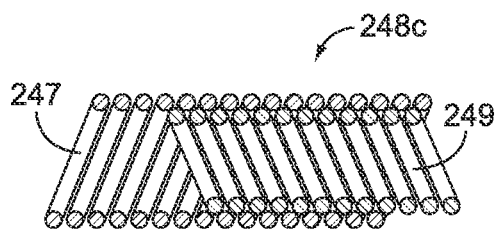
FIG. 56
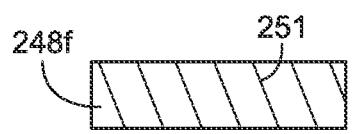
FIG. 57
FIG. 58
FIG. 59
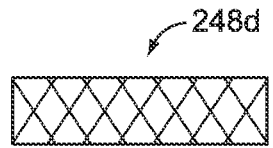
FIG. 60
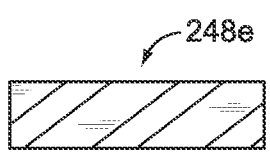
FIG. 61

TISSUE REMOVAL TOOLS AND METHODS OF USE

The present application claims the benefit of U.S. Provisional Application Ser. No. 61/140,401, filed Dec. 23, 2008, which is incorporated herein by reference.

FIELD OF THE INVENTION

The present invention generally relates to apparatus and methods employed in minimally invasive surgical procedures to cut and remove tissue from a patient and, more particularly, to apparatus and methods that may be utilized in a minimally invasive, e.g. endoscopic, surgical procedure to cut and remove tissue from an intervertebral disc.

BACKGROUND OF THE INVENTION

A major cause of chronic, and often disabling, back pain is disruption or degeneration of an intervertebral disc. The spine is comprised of bony vertebrae separated by intervertebral discs. Each intervertebral disc connects adjacent vertebrae and forms a joint that allows movement of the vertebral column. An intervertebral disc is generally divided into two regions: the nucleus pulposus and the annulus fibrosus. The nucleus pulposus is a gelatinous-like tissue that lies at the center of the disc and provides a cushion between adjacent vertebrae. The annulus is made up of collagen fibers that form concentric lamellae that surround and contain the nucleus pulposus.

There are many causes of disruption and degeneration of intervertebral discs, which can be broadly categorized as mechanical, genetic and biochemical. Mechanical damage includes herniation in which a portion of the nucleus pulposus projects through a fissure or tear in the annulus fibrosus. Genetic and biochemical causes usually result from changes in the biochemical processes of a disc. Such changes can be attributed to genetic disorders or environmental influences. Degenerative disc condition is commonly caused by a change in the biochemical process of an intervertebral disc. Such degeneration is a progressive process that usually begins with a decrease in the ability of the nucleus pulposus to absorb water. With a loss of water content, the nucleus becomes dehydrated, resulting in a decrease of internal disc hydraulic pressure, and ultimately to a loss of disc height. This loss of disc height can cause the annulus to buckle, eventually resulting in annular fissures and ruptures. Herniation occurs when a rupture leads to protrusion of the nucleus pulposus through the annulus.

Furthermore, disc height plays an important role in the functionality of the intervertebral disc and spinal column, and changes in disc height can have both local and wider effects. On the local (or cellular) level, decreased disc height may result in increased pressure in the nucleus pulposus, which can lead to a decrease in normal cell operation and an increase in cell death and disintegration. In addition, increases in intradiscal pressure may create an unfavorable environment for fluid transfer into the disc, which can cause a further decrease in disc height.

Decreased disc height also results in significant changes in the larger mechanical stability of the spine. With decreasing height of the disc, the facet joints bear increasing loads and may undergo hypertrophy and degeneration. Decreased stiffness of the spinal column and increased range of motion resulting from loss of disc height can lead to further instability of the spine, as well as back pain.

Several disc defects may be treated by implantation of a prosthetic into the nuclear space of the intervertebral disc. Some procedures that may include insertion of a prosthetic into the disc are spinal fusion and disc repair and replacement. Prior to implantation of most prosthesis, a discectomy is often performed to prepare the nuclear space for implantation of the prosthetic and, when spinal fusion is desired, to facilitate bony fusion between the vertebral bodies. Some implantation procedures may require a total discectomy in which the majority (and usually all) of the volume of the nucleus pulposus is removed. Others may require a partial discectomy in which only a portion of the nucleus pulposus is removed.

Traditionally, discectomy procedures are performed with the use of simple manual instruments, such as curettes, which are cupped scrapers with a variety of end configurations, pituitary rongeurs, which are jaw like gripping or cutting members, and rasps, which include a rough surface that is employed to roughen and scrape endplate tissue of adjacent vertebrae. For a typical posterior surgical approach, an incision is made through the back of a patient and access to the disc space is achieved. The manual instruments are then inserted through the access to the intervertebral disc requiring treatment. The curettes and rongeurs are used to cut, tear, and remove nucleus pulposus tissue one piece at a time, and the rasps are utilized to roughen or scrape the endplates of adjacent vertebrae.

There are some significant limitations associated with performing a discectomy with these manual instruments. For example, since the disc tissue is cut and removed a piece at a time, dozens of repeated cycles of insertion and removal of the traditional instruments are required to remove the desired amount of tissue. The repeated cycles increase the risk of associated nerve damage and the amount of trauma to the surrounding tissue. Additionally, guidance of the traditional instruments is largely controlled by the dexterity of the surgeon, and even with the most skilled surgeons, repeated precise placement of such instruments is a challenge. Furthermore, because of the geometric configuration of traditional instruments and the limited work space associated with intervertebral disc procedures, it can be difficult to adequately remove the required amount of material from the nuclear space. This is particularly the case with a unilateral (one of the more preferred) access of the disc space, where the contralateral half of the disc is significantly more difficult to reach. Finally, surgeons typically use traditional instruments without being able to see the tissue being removed. Thus, the surgeon must be able to distinguish nucleus tissue from annulus tissue and bone tissue by "feel." Thus, if the surgeon has a difficult time distinguishing between these tissues, serious damage can be done to the annulus of the disc or the vertebral bodies.

Other methods and techniques have been developed for performing discectomy procedures. However, these methods and techniques also have limitations and risks associated with their use. Accordingly, there remains a need for improved discectomy devices and methods.

SUMMARY

The present disclosure is directed to tissue manipulation systems and tools that can be used to disrupt tissue of a patient, such as by cutting and/or scraping. The tissue manipulation system and tools also may be used to remove tissue from a patient. The tools disclosed herein are particularly useful for performing discectomy procedures and preparing the nuclear space for prosthetic implantation and spinal fusion. The tools described herein may be used individually for their intended purpose or together in the system.

One aspect of the present disclosure relates to an intervertebral disc preparation system for preparing an intervertebral disc space for implantation of a prosthetic device or for a fusion procedure. The system includes a guide member that has a proximal end portion and a distal end portion. The distal end portion of the guide member is changeable from a deployment configuration for insertion into the intervertebral disc space to a deployed configuration within the intervertebral disc space. In one embodiment, the deployment configuration comprises a generally straight or linear configuration and the deployed configuration comprises a pre-defined less linear configuration. The less linear deployed configuration may be a generally arcuate configuration, such as a generally circular, elliptical or spiral configuration.

The system also may include at least one elongated member that has a distal end portion and an outer surface. The elongated member may be a pusher member, for example, a hollow delivery or drive shaft. The elongated member is moveable longitudinally along the guide member. In one embodiment, the elongated member is moveable back and forth along the guide member.

The system further includes at least one tissue manipulator for manipulating tissue within the intervertebral disc space. The tissue manipulator may be a tissue manipulating element, such as a tissue cutter, a tissue scraper or a tissue extractor. The tissue manipulator is associated with the distal end portion of the elongated member and has at least one tissue manipulation surface that is spaced in a radial direction from the outer surface of the elongated member.

Another aspect of the present disclosure relates to a system for removing tissue from an intervertebral disc space. The system includes a guide member having a proximal end portion and a distal end portion. The distal end portion of the guide member is changeable from a generally linear deployment configuration for insertion into the intervertebral disc space to a pre-defined less linear deployed configuration within the intervertebral disc space. The pre-defined less linear configuration may be an arcuate configuration, such as a generally circular, elliptical or spiral configuration.

The system also includes at least one tissue disruptor for disrupting tissue within or adjacent to the intervertebral disc space. The tissue disruptor may be, for example, a tissue cutter or tissue scraper. The tissue disruptor is insertable into the intervertebral disc space and is longitudinally moveable along the guide member. In one embodiment, the tissue disruptor is moveable back and forth along the guide member to disrupt tissue.

The system further includes at least one tissue extractor for capturing and removing disrupted tissue from the intervertebral disc space. The tissue extractor is insertable into the intervertebral disc space and is longitudinally moveable along the distal end portion of the guide member.

In another aspect, the present disclosure relates to a method of disrupting and removing tissue from an intervertebral disc space. The method includes guiding a tissue disruptor into an intervertebral disc space along a pre-defined path. The tissue disruptor is employed to disrupt tissue within or adjacent to the intervertebral disc space. After the tissue has been disrupted, the tissue disruptor is removed from the intervertebral disc space. A tissue extractor is guided into the intervertebral disc space along the pre-defined path and is used to remove tissue from the intervertebral disc space.

These and other aspects of the present disclosure are set forth in the following detailed description. In that respect, it should be noted that the present invention includes a number of different aspects which may have utility alone and/or in combination with other aspects. Accordingly, the above summary is not an exhaustive identification of each such aspect that is now or may hereafter be claimed, but represents an overview of the present invention to assist in understanding the more detailed description that follows. The scope of the invention is as set forth in the claims now or hereafter filed.

BRIEF DESCRIPTION OF THE FIGURES

In the course of this description, reference will be made to the accompanying drawings, wherein:

FIG. 7 is a top view of another embodiment of a guide member constructed in accordance with the present disclosure;

FIG. 8 is a side view of another embodiment of a guide member constructed in accordance with the present disclosure and shown deployed within an intervertebral disc;

FIG. 9 is a top view of another embodiment of a guide member constructed in accordance with the present disclosure;

FIG. 10 is a top view of another embodiment of a guide member constructed in accordance with the present disclosure;

FIG. 26 is a schematic illustration of one embodiment of a tissue manipulation tool rotating about a guide member within the nuclear space of a disc;

FIG. 27 is a perspective view of an other tissue manipulation tool constructed in accordance with the present disclosure;

FIG. 28 is a side view of the tissue manipulation tool of FIG. 27;

FIG. 29 is a front end view of the tissue manipulation tool of FIG. 27;

FIG. 30 is top view of yet another embodiment of a tissue manipulation tool constructed in accordance with the present disclosure and shown deployed within a disc space;

FIG. 35 is a top view of a tissue manipulation tool deployed along the guide member of FIG. 34;

FIG. 36 is a cross-sectional view of the tissue manipulation tool and guide member taken along line A-A of FIG. 35;

FIG. 37 is a top view of another embodiment of a tissue manipulation tool constructed in accordance with the present disclosure and shown deployed within a disc space;

FIG. 52 is a top view of an elongated member showing exemplary tine configurations;

FIGS. 53-55 are side views of alternative embodiments of tissue manipulation elements;

FIG. 56 is a partial cross-sectional view of one embodiment of an internal support members; and FIGS. 57-61 are side views of alternative embodiments of internal support members.

DETAILED DESCRIPTION

Figure 1:
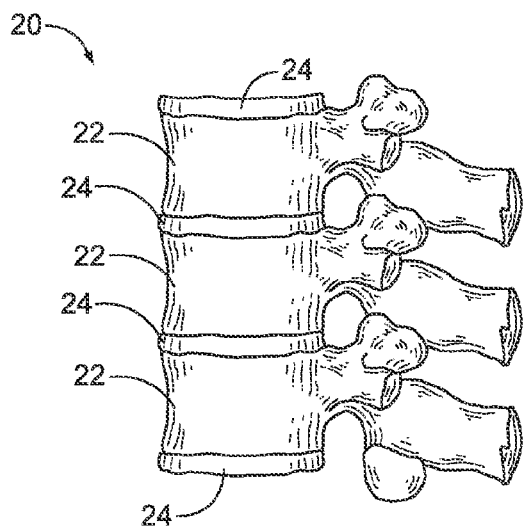
FIG. 1 is a side view of a healthy vertebral (spinal) column.

FIG. 1 illustrates a section of a healthy vertebral (spinal) column, generally designated as 20. Vertebral column 20 includes vertebrae 22 and intervertebral discs 24 separating adjacent vertebrae. Intervertebral discs 24 connect the adjacent vertebra 22 together, providing a joint between the vertebrae that allows movement and flexing of the vertebral column 20. Intervertebral discs 24 also provide a cushion between the adjacent vertebrae 22.

Figure 2:
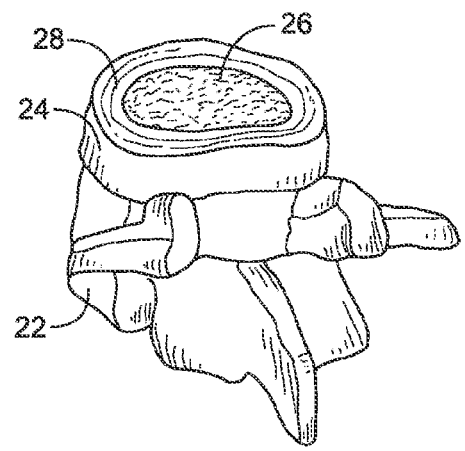
FIG. 2 is a perspective view of an intervertebral disc and its associated inferior vertebra.

FIG. 2 illustrates a perspective view of one of the intervertebral discs 24 and an associated inferior vertebra 22. The intervertebral disc 24 includes a nucleus pulposus 26 surrounded by an annulus fibrosus 28. The nucleus pulposus 26 is a gelatinous-like material that provides cushioning between adjacent vertebrae. The annulus fibrosus 28 is made up of tougher fibrous material that contains the nucleus pulposus 26 in the nuclear space.

Turning now to the tissue manipulation members or tools, such as the tissue disruption and removal tools of the present disclosure, the tools and methods described herein can be utilized in any number of surgical procedures to cut or otherwise disrupt and remove tissue from a patient, but are particularly well suited for performing endoscopic discectomy procedures and preparing intervertebral discs for prosthetic implantation and spinal fusion. For example, the tissue manipulation tools may be utilized in minimally invasive procedures that are conducted through an access port that has a diameter of between about 0.2 inches (5 mm) and about 0.4 inches (10 mm). The tissue manipulation tools disclosed herein may be made from materials that are visible under x-ray, fluoroscopy or any other suitable imaging system. The tissue manipulation tools may also be made of disposable materials and configured for single use applications. Alternatively, the tissue manipulation tools may be configured as multiple use tools. The manipulation tools may be manually operated or operated by an automated apparatus.

The discectomy and disc preparation tools of the present disclosure generally include a guide member and one or more tissue manipulation devices, such as tissue disruption tools and tissue extraction tools, that can be used in conjunction with each other to cut and remove intervertebral disc tissue. Some examples of tissue disruption tools may include tissue cutting and scraping tools. When in use, the guide member is inserted through the annulus fibrosus and into the nuclear space of an intervertebral disc to provide a generally prescribed pathway for the cutting, scraping and tissue extraction tools to follow. The tools are guided by the guide member, unless the tools are an integral part of the guide member, through the annulus fibrosus and along the generally predefined path into and through the nucleus pulposus region, sometimes referred to as the nuclear space. As each tool is guided by the guide member through the nuclear space, the tool performs its function, i.e., disrupts, cuts, scrapes, grasps or engages tissue, or can be manipulated to perform its function.

Figure 3:
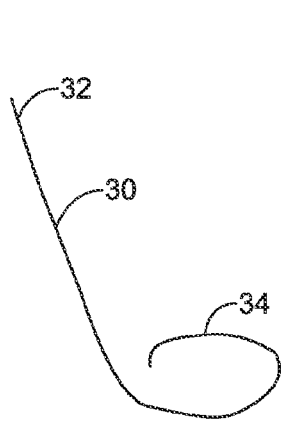
FIG. 3 is a top view of one embodiment of a guide member constructed in accordance with the present disclosure.

FIG. 3 illustrates one embodiment of a guide member 30 that may be comprised of an elongated member, such as a wire, thread or ribbon. The guide member 30 includes a proximal end portion 32 and a distal end portion 34. The distal end portion 34 of the guide member 30 is the portion that is inserted into the nuclear space of the intervertebral disc to provide a structure that can guide the above mentioned cutting, scraping and extraction tools along a desired, pre-defined path through the nuclear space. Preferably, the shape of the distal end portion 34 results in a path that guides the tools to all of the desired locations of the nuclear space required for a particular application. In the embodiment illustrated in FIG. 3, the distal end portion 34 of guide member 30 has a generally elliptical-shaped configuration that can generally follow along the inner wall of the annulus. Alternatively, the guide member can be shaped in an arc or arcuate shape. In one embodiment, the arc shaped guide member is configured to guide the tools from at least the side of the disc where guide member is accessed (ipsilateral) to the opposite side of the disc (contralateral). By repositioning the guide member between anterior and posterior positions, the arc-shaped guide member can guide the tools to all desired locations of the nuclear space. Preferably, the arc shaped guide member is configured so that only moderate repositioning is required to guide the tools to the desired locations for a particular procedure.

Preferably, at least the distal end portion 34 of the guide member 30 is made of a shape memory material, such as a pseudoelastic material, for example Nitinol (NiTi) or other suitable alloy (Cu—Al—Ni, Ti—Nb—Al, Au—Cd, etc.). In other embodiments, the distal end portion can be made from a shape memory polymer. Due to the shape memory characteristics, the guide member 30 can be bent or deformed into a generally linear or straight configuration by inserting or drawing the guide member into a deployment or working cannula. As used herein the term "linear" can refer to perfectly straight or having slight bends or zigzags. When located within the cannula, the guide member 30 takes on and is constrained in the generally linear configuration, so that the guide member can be translated through the cannula for deployment into a patient. When the distal end portion of the guide member exits the cannula, it returns to its generally elliptical-shaped configuration. Thus, because of the guide member's inherent tendency to return to a particular pre-defined shape (i.e., shape memory or pseudoelastic characteristics), the guide member can be deformed prior to or during deployment into a treatment site and then returned to its original shape within the treatment site.

Figure 4:
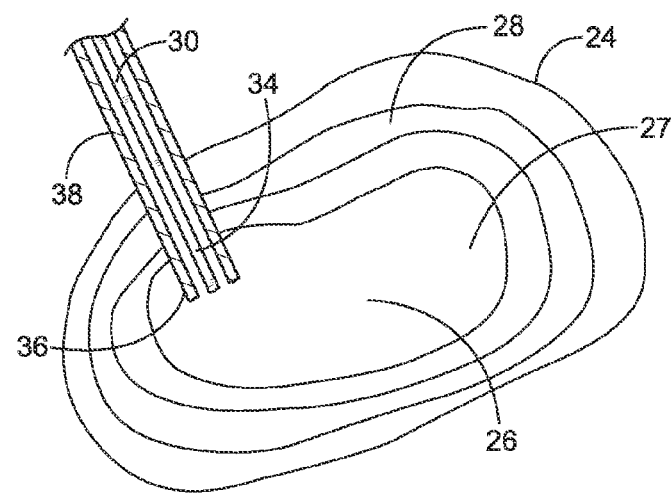
FIG. 4 is a cross-sectional view of an intervertebral disc having a deployment cannula inserted through the annulus fibrosus and partially into the nuclear space.
Figure 5:
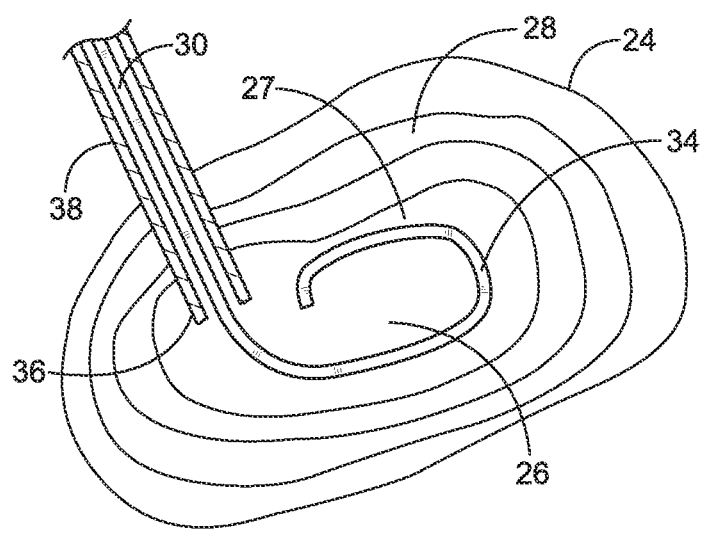
FIG. 5 is a cross-sectional view of the intervertebral disc of FIG. 4, shown with a guide member inserted into the nuclear space.

Referring to FIGS. 4 and 5, to deploy the distal end 34 of the guide member 30 into an intervertebral disc 24, the distal end portion 36 of a deployment cannula 38 is inserted through the annulus fibrosus 28 and into or adjacent the nucleus pulposus 26 in nuclear space 27. The insertion of the cannula 38 through the annulus can be through a surgical incision or a pre-existing fissure. Additionally, the deployment cannula 38 can access the intervertebral disc 24 through any suitable access approach. For instance, access for the deployment cannula 38 can be gained through either a posterior lumbar approach, a transforaminal lumbar approach, or a lateral approach. Some procedures may require the deployment of two guide members. In such circumstances, two cannulas can be employed wherein, for example, the first cannula accesses the intervertebral disc from one side, and the second cannula accesses the disc from the other side.

When the discectomy and disc preparation procedures described herein are utilized to prepare the intervertebral disc for endoscopic prosthetic implantation, the size of the surgical access site required for inserting the deployment cannula 38 into the intervertebral disc 24 is preferably not larger than the size of the surgical access site required for implantation of the prosthetic. One of the advantages of utilizing a prosthetic that can be implanted by a minimally invasive endoscopic procedure is that there is less trauma and damage caused to the surrounding tissue. If the access site required for performing a discectomy (or pre-implantation preparation of a disc) is larger than what is required for the endoscopic implantation procedure, then the above-mentioned benefits of the minimally invasive procedure can be diminished. This is especially true when the same access site is used for both the disc preparation procedure and the prosthetic implantation procedure. Accordingly, one of the advantages provided by the tools and procedures described herein are that the access sites needed to perform the procedures are relatively small and similar in size to that required for several of the endoscopic prosthetic implantation procedures. Preferably, the access site has an outer diameter between about 4 mm and about 10 mm. In one embodiment the access site has an outer diameter of about 8 mm. It will be understood that depending on the procedure being preformed that the accesses sites could be larger or smaller than the above range.

Once the deployment cannula 38 is in the desired location, which can be verified through fluoroscopy, the guide member 30 in a generally linear configuration is advanced through the cannula 38. Turning now to FIG. 5, upon exiting the distal end portion 36 of the cannula 38, the distal end portion 34 of guide member 30, by change of configuration, transitions into its generally arcuate shape, such as the partial elliptical-shaped configuration shown. When the guide member 30 is manufactured from materials that are readily visible under fluoroscopy, such as nitinol, the surgeon can use fluoroscopy to ensure that the guide member is delivered along the desired path and is positioned at the desire location. Additionally, the guide member 30 should have sufficient column strength to penetrate the nucleus pulposus 26 and sufficient rigidity to provide a guiding force for the cutting, scraping and extraction tools that will be translated along the guide member 30. The guide member 30 may have different cross-sectional shapes, such as circular, rectangular or other suitable shapes. In one embodiment, the cross-sectional width of the guide member 30, which may be the diameter, is between about 0.04 inch (1 mm) and about 0.1 inch (2.5 mm). The cross-sectional width may also be larger or smaller than this range depending on the particular procedure. Additionally, the size of the guide member may vary along its length to optimize its ability to penetrate only the nuclear tissue while still providing sufficient guiding force for the tools. Furthermore, the distal tip of the guide member may have a feature that facilitates transition through the disc tissue. For example, the guide member could include a blunt or rounded distal end portion that allows it to penetrate soft nucleus material, but prevents it from penetrating the tougher annulus tissue. The dimensions of the ball tipped distal end of the guide member can be varied depending of the column strength of the guide member to reduce the risk of penetration of the guide member into the annulus tissue. Conversely, if desired, the distal tip of the guide member could be configured to penetrate annulus tissue.

Depending on the particular procedure, the location and amount of tissue to be removed, the guide member can have a variety of shapes or configurations, including but not limited to full or partial circular and elliptical shapes, spiral shapes and wavy shapes, and other curved shapes or any other suitable shapes. Additionally, the guide member can have a two dimensional configuration, such as those shown in FIGS. 5, 7, 9 and 10, or a three-dimensional configuration, such as that shown in FIG. 8. FIGS. 7-10 illustrate some of the possible alternative configurations of the guide member. In FIG. 7, the distal end portion 40 of the guide member 42 has a two-dimensional spiral shape that lies in a single plane. In FIG. 8, the distal end portion 44 of guide member 46 has a three-dimensional coiled or helical shape that can have one or more loops and can span from the superior endplate 48 of the adjacent lower vertebral body 50 to the inferior endplate 52 of the adjacent upper vertebral body 54. FIGS. 9 and 10 shows guide members 56 and 58 that have a looped configuration. Guide member 56 of FIG. 9 has a distal end portion 60 that includes a continuous loop that loops back into the cannula 62. Guide member 58 of FIG. 10 includes a distal end portion 64 having a conjoined loop wherein the distal tip 66 of the guide member includes an eyelet 68 that is connected to the distal end portion 64 of the guide member 58.

Figure 6:
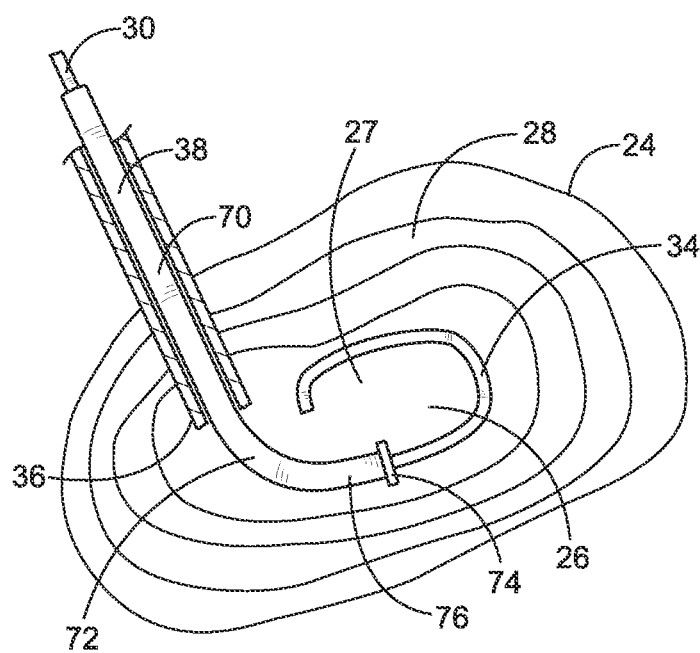
FIG. 6 is a cross-sectional view of the intervertebral disc of FIG. 4, shown with a tissue manipulation tool deployed over the guide member.

Turning now to FIG. 6, after the distal end portion 34 of the guide member 30 is deployed into the nuclear space 27 of intervertebral disc 24, a tissue manipulation tool, such as cutting tool 70, is advanced distally along the guide member 30 and through the deployment cannula 38. When the cutting tool 70 is advanced out of the distal end portion 36 of the deployment cannula 38, it enters the nuclear space 27 and translates along the distal end portion 34 of the guide member 30. The distal end portion 34 of the guide member 30 guides the cutting tool 70 along a predetermined path through the nuclear space 27. Guiding the cutting tool 70 in this manner can provide greater assurance that the cutting tool will reach all of the desired locations for the particular procedure and reduces the risk of accidental injury to the annulus and vertebrae. Preferably, the relationship between the cutting tool 70 and the guide member 30 allows the cutting tool to be translated back and forth along the distal end portion 34 and rotated thereabout. As the cutting tool 70 translates along, and optionally rotates about, the guide member 30, it cuts, tears and/or otherwise disrupts the tissue of the nucleus pulposus 26 located in nuclear space 27. Alternatively, if the design of the tissue cutting, disruption, or extraction tool has a preferred mode of operation in just one rotational direction, the proximal handle of the tool may incorporate a one-way ratcheting or clutch mechanism such that it can rotate in only one direction.

In the embodiment of the tissue manipulation or cutting tool 70 shown in FIG. 6, the cutting tool includes an elongated member, such as pushing member 72 which may be, for example, a hollow drive or delivery shaft. The cutting tool 70 also includes a tissue manipulator or manipulation element, such as tissue cutter or cutting element 74, located at the distal end portion 76 of the pushing member 72. The cutting tool 70 is removably associated with the guide member 30 by inserting the guide member 30 into a passageway through pushing member 72 and advancing the cutting tool 70 axially or longitudinally over the guide member 30. The pushing member 72 should have sufficient column strength so as to be distally advanced longitudinally along the guide member 30 and penetrate through nucleus tissue. Preferably, the pushing member 72 also is pullable with minimal stretchability so that is can be easily translated back and forth longitudinally along the guide member 30 and easily withdrawn from the treatment site. Additionally, at least the distal end portion 76 of the pushing member 72 should have sufficient flexibility to translate along the distal end portion 34 of the guide member 30. Optionally, the pushing member 72 can also translate rotation forces from the proximal end (not shown) to the distal end 76, preferably in both clockwise and counterclockwise directions. Preferably, the length of the pushing member 72 is such that manipulation of the proximal end of the pushing member is quickly translated to the distal end portion 76. Also, the pushing members or shafts have a length sufficient to deliver the tissue manipulation elements through a delivery cannula, if one is used, and to the treatment site. In one embodiment, the pushing member is between about 3 cm and about 8 cm in length, and in another embodiment, the pushing member is about 30 cm in length.

The elongated members or pushing members are preferably constructed from a radiopaque material that is visible under fluoroscopy to facilitate observation of its advancement relative to the guide member. The pushing members may also include depth markings on their outer surfaces that allow tracking of advancement into the patient by the naked eye. The internal diameter of the pushing member may be large enough to allow insertion and translation along the guide member. In one embodiment the internal diameter is about 0.07 inch (1.78 mm). The outer diameter of the pushing member may vary and, preferably, is of a size that allows the pushing members to be advanced along the guide member without bucking and/or kinking. In one embodiment, the pushing member has an outer diameter of about 0.2 inch (5.1 mm).

Figure 11:
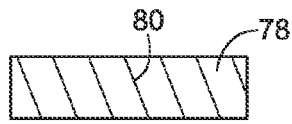
FIG. 11-15 are partial side views of different embodiments of pushing members constructed in accordance with the present disclosure.
Figure 12:
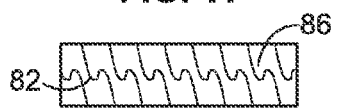
Figure 13:
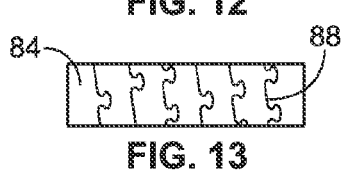
Figure 14:
Figure 15:
Figure 16:
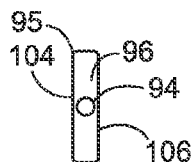
FIG. 16 is a front end view of one embodiment of a tissue manipulation element constructed in accordance with the present disclosure.

Suitable pushing members or delivery shafts can include, but are not limited to, laser cut hypotubes, multi-layer extrusions shafts that are braided or ribbon reinforced, or counter-wound hollow shafts that include tight inner and outer springs wound in opposite directions. FIGS. 11-13 illustrate some suitable laser cut hypotube shafts, such as a laser cut stainless steel hypotube. The shaft 78 illustrated in FIG. 11 includes a simple spiral cut 80 that provides translation of torque, but only in one direction. The shafts 82 and 84 illustrated in FIGS. 12 and 13 have more complex cut patterns 86 and 88 that can transmit torque in both directions. The cut patterns of these shafts can vary in width and pitch to optimize mechanical performance and the ability to track over guide members of varying size and shape. FIGS. 14 and 15 illustrate exemplary embodiment of multi-layer extruded shafts 90 and 92 with braided or ribbon reinforcement. The multi-layer extruded shafts are reinforced with metal wire or ribbon to provide a flexible, but torqueable shaft.

Optionally, the proximal end portion of the hollow pushing member or shaft can be operatively connected to a suction source to provide a suction force at the distal end portion of the shaft. The suction force can be used to draw tissue to be disrupted toward the cutting element. Additionally, the suction force can be used to draw disrupted tissue into the distal end portion of the shaft and through the shaft to remove the disrupted tissue from the intervertebral disc.

Turning now to the tissue manipulators or manipulating elements of the tissue manipulation tool. The tissue manipulation elements may be associated with the distal end portion of the elongated pushing member and in one embodiment can be attached thereto. Preferably, the tissue manipulators or manipulating elements have a shape that is conducive to translating along the curved path of the distal end portion of the guide member and/or have sufficient flexibility that allows translation along the curved path. The manipulation elements also have sufficient rigidity to effectively disrupt tissue, such as by cutting or scraping, and/or capture and remove tissue.

When the tissue manipulation elements are tissue disruptors or disruption elements, such as cutting and/or scraping elements, the tissue disruptors may include one or more blades or bladed edges having tissue manipulation surfaces that are suitable for contacting and cutting and/or scraping intervertebral disc tissue. The tissue manipulation surfaces are preferably particularly well suited for cutting nucleus pulposus tissue and scraping vertebral endplates adjacent to the disc space. The tissue manipulation surfaces may be spaced or at least partially spaced in a radial direction from the outer surface of the pushing member and/or from the central axis of the tissue manipulation element and/or from the rotational axis of the manipulation element when the manipulation element is configured to rotate. The profile of the blades may be flat or curved and the shape of the blades C-shaped, L-shaped or otherwise shaped. Additionally, the blades or cutting edges can be serrated or smooth. The blades also can be substantially rigid at or near the point of attachment of the cutting element to the pushing member and more flexible toward the distal ends of the blades so that the blades do not inadvertently damage the annulus or the endplates of adjacent vertebra.

Figure 17:
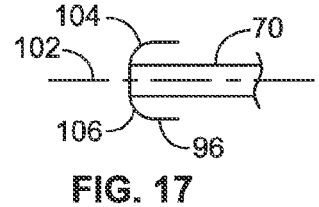
FIG. 17 is a side view of the tissue manipulation element of FIG. 16.
Figure 18:
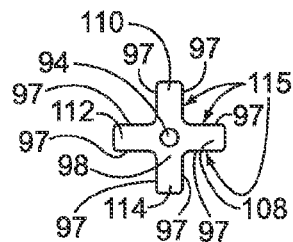
FIG. 18 is a front view of another embodiment of a tissue manipulation element constructed in accordance with the present disclosure.
Figure 19:
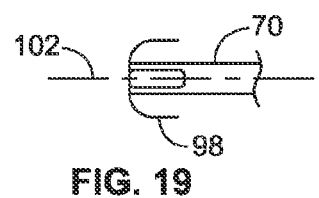
FIG. 19 is a side view of the tissue manipulation element of FIG. 18.
Figure 20:
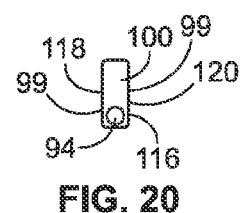
FIG. 20 is a front view of yet another embodiment of a tissue manipulation element constructed in accordance with the present disclosure.
Figure 21:
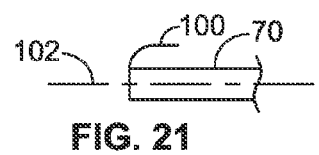
FIG. 21 is a side view of the tissue manipulation element of FIG. 20.

FIGS. 16-21 show examples of tissue manipulation or cutting elements 96, 98, 100 that can be associated with the distal end portion of the pushing member of a tissue manipulation tool, such as be attachment thereto. The illustrated embodiments of the tissue cutters or cutting elements of these figures include a hole or passageway 94 for passage of the guide member therethrough. The passage of the guide member through the hole allows the cutting elements to rotate about the guide member. Referring to FIGS. 17, 19 and 21, the axis of rotation of each cutting element, which in some embodiment may also be the central axis of the cutting element, is designated as 102. Referring to FIG. 26, as the cutting tool 70 is advanced longitudinally over the distal end portion 34 of guide member 30, the proximal end portion 74 of pushing member 70 can be rotated by hand or machine. The rotational forces are translated along the pushing member 70 to the distal end portion 76 of the pushing member 72, resulting in rotation of cutting element 74 as indicated by arrow 75.

Referring back to FIG. 16, the tissue cutter or cutting element 96 has a generally elongated front face in which the passageway 94 for receiving the guide member is located therethrough. As shown in FIG. 17, the cutting element 96 may be a U-shaped strip of material having a thin, flat profile. Alternatively, the cutting element 96 may have a thicker profile or a block-like configuration. Edges 104 and 106 have tissue manipulation surfaces 95 that contact and cut or otherwise disrupt tissue. The tissue manipulation surfaces are spaced or at least partially spaced in a radial direction from the outer surface of the pushing member 70. The tissue manipulation surfaces may also be spaced in a radial direction from the axis of rotation 102 and/or from the central axis of the cutting element. The edges 104 and 106 may be bladed edges or sharp edges that are designed to cut or otherwise disrupt nucleus pulposus tissue as the cutting member 96 is advanced along and/or rotated about the guide member.

The cutting element 98 of FIGS. 18 and 19 has a generally cruciform shape with the passageway 94 located through the center of the cruciform. Cutting element 98 may have a thin profile or may have a block-like configuration Each appendage 108, 110, 112, 114 of the cruciform includes one or more bladed edges 115 having tissue manipulation surfaces 97 that contact and cut or otherwise disrupt nucleus tissue as the cutting element 98 is advanced along and rotated about the guide member. As shown in FIG. 19, the tissue manipulation surfaces are spaced or at least partially spaced in a radial direction from the outer surface of the pushing member. The tissue manipulation surface may also be radially spaced from the axis of rotation 102 and/or from the central axis of cutting element 98.

Cutting element 100 of FIGS. 20 and 21 may be an L-shaped strip of material having a thin profile. Alternatively, cutting element 100 may have a thick profile or a block-like configuration. The passageway 94 for receiving the guide member is located through the front face 116 of the cutting element 100. Similar to the other cutting elements, cutting element 100 includes edges 118 and 120 having tissue manipulation surfaces 99 that contact and cut or otherwise disrupt nucleus tissue as the cutting element is advanced along and rotated about the guide member. Edges 118 and 120 may be bladed or sharpened to assist in cutting the tissue. Additionally, as shown in FIG. 21, the tissue manipulation surfaces are spaced or at least partially spaced in a radial direction from the outer surface of the pushing member and/or from the axis of rotation.

Figure 22:
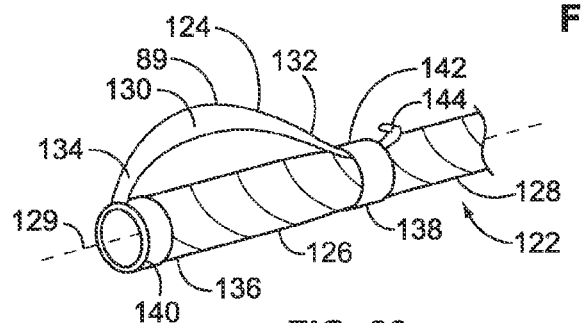
FIG. 22 is a perspective view of another embodiment of a tissue manipulation element constructed in accordance with the present disclosure.
Figure 23:
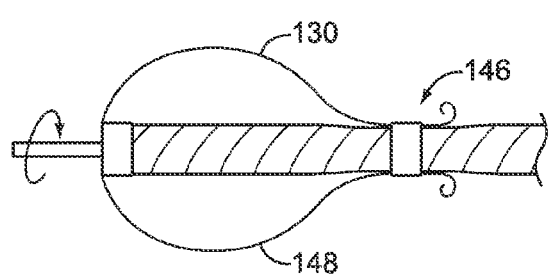
FIG. 23 is a side view of a further embodiment of a tissue manipulation element constructed in accordance with the present disclosure.

FIGS. 22-25 illustrate other embodiments of tissue manipulation tools, such as the illustrated cutting tools. In the embodiments shown the cutting element includes as least one outwardly extending curved blade that is attached to the distal end portion of the pushing member at two locations. The blade includes at least one tissue manipulation surface 89 that contacts and cuts or otherwise disrupts tissue. The tissue manipulation surface is spaced or at least partially space in a radial direction from the outer surface of the pushing member 128. The tissue manipulation surface also may be radially spaced from the axis of rotation 129 and/or the central axis of cutting tool 122. Referring to FIG. 22, the cutting tool 122 includes a cutting element 124 attached to the distal end portion 126 of pushing member 128, which can be any of the shafts described herein or any other suitable pushing member. The cutting element 124 includes a blade 130 that has a proximal end portion 132 and a distal end portion 134. The distal end portion 134 of blade 130 can be attached at or near the distal tip 136 of the shaft 128 and the proximal end portion 132 of the blade 130 can be attached to the distal end portion 126 of the pushing member 128 at 138. In the illustrated embodiment, the distal end portion 134 of the blade 130 is affixed to a first collar 140 attached to the distal tip 136 of the pushing member 128. The proximal end portion 132 of the blade 130 is slidably attached to a second collar 142 located proximal the first collar 140. The proximal end portion 132 of the blade 130 is slidably located between the second collar 142 and the pushing member 128. The proximal tip 144 of the blade 130 includes a bent or curled tail section that engages the second collar 142 to prevent the proximal end portion 132 of blade 130 from sliding distally past the second collar 142. Thus, the proximal end portion 132 of blade 130 is slidably trapped between the pushing member 128 and the second collar 142. FIG. 23 illustrates an alternative embodiment of the cutting tool in which the tool 146 includes a first blade 130 and a second blade 148, in a two or opposing dual blade configuration.

Figure 25:
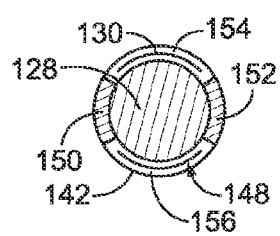
FIG. 25 is a cross-sectional view of the tissue manipulation element of FIG. 23.

FIG. 25 shows one embodiment of the slip fit attachment between the proximal ends of blades 130 and 148 and the second collar 142 for the dual blade cutting tool shown in FIG. 23. The second collar 142 can be attached to opposed sides of the pushing member 128 at attachment locations 150 and 152, leaving spaces or slots 154 and 156 between the collar 142 and the pushing member 128. The collar 142 can be attached to the pushing member 128 in any suitable fashion, such by welding, solder or with the use of suitable adhesives. The proximal end of blade 130 is located in slot 154 and proximal end of blade 148 is located in slot 156. The proximal tips of the blades 130 and 148 can be pre-curled or curled after insertion into slots 154 and 156.

Figure 24:
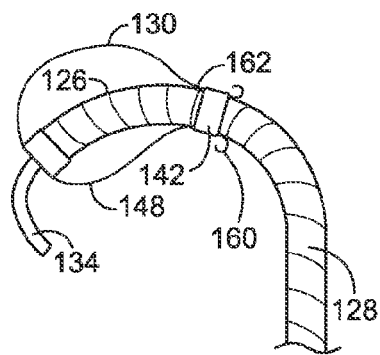
FIG. 24 is a top view of the tissue manipulation element of FIG. 23.

Referring to FIG. 24, the slip fit connection between the blades 130 and 148 and the pushing member 128 enhances the cutting tool's ability to translate over the curved portions of the distal end portion 34 of guide member 30. As the distal end portion 126 of pushing member 128 translates over the distal end portion 34 of the guide member 30, the proximal end portion 160 of blade 148, located on the inside of the curve, moves proximally away from collar 142 and the proximal end portion 132 of blade 130, located on the outside of the curve, moves distally until it engages collar 142. Additionally, referring back to FIG. 23, the cutting tool can also be rotated about guide member 30.

Figure 31:
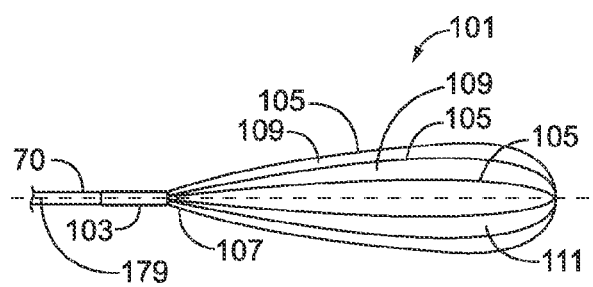
FIG. 31 is a side view of another embodiment of a tissue manipulation element constructed in accordance with the present disclosure.

FIG. 31 illustrates another embodiment of a tissue manipulation element 101 that may be used for cutting tissue and/or capturing tissue for removal. Tissue manipulation element 101 includes a tubular member 103 and a plurality of blade members 105 having tissue manipulation surfaces. The blade members 105 may be elongated members, such as ribbons or wires. The ends 107 of the blade members 105 are connected to the tubular member 103. The blade members 105 may be flat elongated members or rounded elongated members. Additionally, the blade members 105 may have a variety of surface configurations, such as sharp bladed surfaces, serrated surfaces or blunt surfaces. The blade members 105 form a whisk-like configuration. In the embodiment shown, each of the blade members 105 extends from the tubular member 103 and doubles back to form the whisk-like arrangement. Tissue manipulation element 101 may be located on the distal end of an elongated member or pushing member 70, which may be any of the delivery shafts described herein or any other suitable pushing member. Furthermore, the tissue manipulation surfaces of the blade members 105 are spaced or at least partially spaced in a radial direction from the outer surface of the pushing member. It will be understood that the pushing member does not necessarily need to be directly adjacent to the tissue manipulation surface for such surface to be spaced in a radial direction from the outer surface of the pushing member, and that the tissue manipulation surface can be spaced both laterally and radially from the outer surface of the pushing member. The tissue manipulation surfaces also may be space in a radial direction from the axis of rotation 179 and/or the central axis of the tissue manipulation element 101. The pushing member may be used to guide the tissue manipulation element 101 along the guide member and into and through disc tissue.

When a guide member is utilized to deploy tissue manipulation element 101, the guide member is inserted through a passage of the pushing member and through tubular element 103 and one of the spaces or openings 109 between adjacent blade members 105. In this arrangement, the pushing member may be used to push the tissue manipulation element 101 along the guide member. When the tissue manipulation element 101 is being used as a cutting element, the blade members 105 preferably are sufficiently flexible to accommodate being advanced along the contour of the guide member and yet rigid enough to cut or otherwise disrupt tissue, such as nuclear and/or endplate tissue. Similar to the above described embodiments, rotation of the pushing member results in rotation of the tissue manipulation element 101 about the guide member. As the tissue manipulation element 101 is rotated about a curved portion of a guide member, the blade members 105 on the inside of the curve of the guide member bow outward and engage tissue, while those on the outside of the curve deform into a more straight configuration that slightly engages tissue. As tissue manipulation element 101 is rotated, blade members 105 engage and cut or otherwise disrupt the tissue. Additionally, blade members 105 of tissue manipulation element 101 can be configured so that as the manipulation element 101 rotates, disrupted tissue becomes captured in the inner space 111 generally defined by the blade members 105 for removal of the disrupted tissue. Thus, the tissue manipulation element 101 may be used as a cutting and extracting tool.

When tissue manipulation element 101 is employed as a tissue removal or extraction tool, the tissue manipulation element 101 may be used to capture and remove tissue that has been cut by tissue manipulation element 101. Alternatively, the tissue manipulation tool may be is inserted into the nuclear space to capture and remove tissue that has been previously disrupted by another cutting tool. When used as both a cutting and removing tool, the blade members 105 of tissue manipulation element 101 may be similar to that described above. When used primarily as a tissue removal tool, the blade members 105 of tissue manipulation element 101 can be generally rounded and substantially blunt, so as to reduce the element's ability to cut tissue. As the tissue manipulation element 101 is rotated, previously disrupted tissue becomes captured within the space 111 generally defined by the blade members 105. The rounded blade members 105 of the tissue manipulation element 111 may still disrupt some tissue and the amount of tissue that the blade members 105 disrupt can be controlled by their configuration. When the desired amount of tissue is captured, the tissue manipulation element 101 is removed. The tissue manipulation element 101 can be cleaned and reinserted, or a new unused tissue manipulation element can be inserted to collect more tissue.

In an alternative embodiment, that does not necessarily require the use of a guide member, tissue manipulation element 101 may be located at the distal end portion of a pushing member, such as an elongated rod or shaft, that may be inserted through a cannula and into a treatment site without the use of a guide member. Preferably, the elongated rod can transmit torque applied to the proximal end portion of the elongated rod to the distal end portion of the rod to rotate the tissue manipulation element. In one embodiment, at least the distal end portion of the elongated rod is constructed of a shape memory material, such as nitinol. When constructed from a shape memory material, the distal end portion of the elongated rod may be pre-set into an arcuate or other non-linear configuration that can be straightened into a generally linear configuration to be passed through a cannula for deployment into the treatment site. As the distal end portion of the elongated rod exits the cannula, it returns to its generally non-linear configuration, directing the tissue manipulation element 101 to the desired location.

Figure 32A:
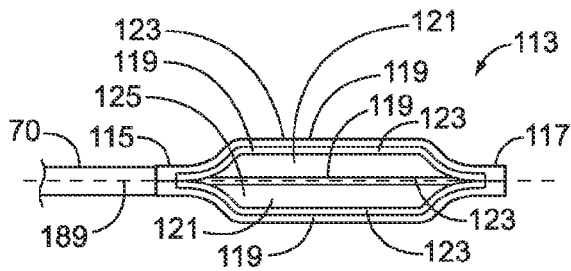
FIG. 32A is a side view of yet another embodiment of a tissue manipulation element constructed in accordance with the present disclosure.

Referring to FIG. 32a, there is shown another embodiment of a tissue manipulation element 113 that may be used as a cutting element and/or a tissue extraction element. Similar to the tissue manipulation elements described above, tissue manipulation element 113 may be located at the distal end of a pushing member 70, such as any of the delivery shafts disclosed herein or any other suitable pushing member. For example, the tissue manipulation element 113 may be located at the distal end portion of a hollow tubular shaft for deployment over a guide member, or tissue manipulation element 113 may be located at the distal end of an elongated rod that may or may not have a predefined shape and does not require the use of a guide member for deployment or placement within a treatment site.

Tissue manipulation element 113 includes a proximal end portion 115, a distal end portion 117 and a plurality of blade members 119 extending therebetween. Preferably, tissue manipulation element 113 includes at least a pair of blade members 119. The blade members 119 may be elongated strips of material that extend generally longitudinally between the proximal end portion 115 and the distal end portion 117. Generally longitudinally extending slots 121 are located between adjacent blade members 119. Preferably, the tissue manipulation element 113 has at least one pair of slots. It should be understood, however, that tissue manipulation element 113 may have any number of slots and that the number of slots depends on the number of blade members. The blade members 119 include a middle section 123 that is bowed outwardly and a tissue manipulation surface that is spaced or at least partially spaced in a radial direction from the outer surface of the pushing member 70. The tissue manipulation surfaces also may be radially spaced from the axis of rotation 189 of the tissue manipulation element and/or the central axis of the tissue manipulation element. The blade members 119 can be of virtually any configuration, such as a flat configuration, a rounded configuration or a combination thereof. Additionally, the surfaces of the blade members are preferably configured for cutting, tearing or otherwise disrupting tissue. As such, the surfaces of the blade members 119 can include sharp or bladed edges, serrations, teeth or the like.

When the tissue manipulation element 113 is configured to be guided into and through tissue of a treatment site by a guide member, the proximal end portion 115 and the distal end portion 117 may be generally tubular shaped members that each end portion 115 and 117 include a passageway for receiving the guide member. The guide member is inserted through the passageway of the proximal end portion 115 through the inner space 125 defined by the blade members 119 and through the passageway of the distal end portion 117 so that the tissue manipulation element 113 can be advanced over the guide member and rotated about the guide member. Preferably, the blade members 119 are constructed of a material that has sufficient flexibility to allow the cutting element 113 to follow along the contour of the guide member. When used a cutting tool, the tissue manipulation element 113 may be rotated about the guide member to cut or otherwise disrupts tissue. In one embodiment, the slots 121 and the blade members 119 can be configured so that the cut tissue is collected within the interior cavity or space 125 generally defined by the blade members 119 for removal from the treatment site.

Figure 32B:
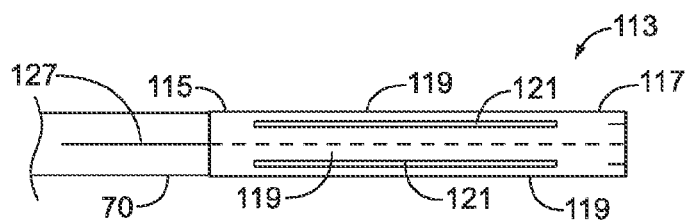
FIG. 32B is a side view of the tissue manipulation element of FIG. 32A shown in a deployment configuration.

In one embodiment, tissue manipulation element 113 may be transformable from a first or deployment configuration to a second or deployed configuration shown in FIG. 32a. It will be understood, however, that the tissue manipulation element 113 is not necessarily transformable and could just have the single configuration illustrated in FIG. 32a. Referring to FIG. 32b, in the deployment configuration, the tissue manipulation element 113 can have a generally tubular or cylindrical shape with the blade members 119 extending in a generally linear or straight configuration. The deployment configuration allows the tissue manipulation element 113 to easily travel through a deployment cannula or through an endoscopic access site. To transform the tissue manipulation element 113 from the deployment configuration to the deployed configuration, the proximal end and distal end portions 115 and 117 are compressed or moved toward each other. As the proximal end and distal end portions 115 and 117 move toward each other, the blade members 119 bow outwardly. In one embodiment, the tissue manipulation element 113 may be made from a shape memory material that has a natural tendency to form the deployed configuration.

In the embodiment shown in FIG. 32b, the tissue manipulation element 113 includes a pull/stop member 127, such as the illustrated wire. The pull/stop member 127 may be an elongated tube or other elongated element. The pull/stop member 127 assists in facilitating the movement of the proximal and distal end portions 115 and 117. In the embodiment shown, the pull/stop member 127 extends through the tissue manipulation element 113 and is attached to the distal end portion 117 of the tissue manipulation element. To facilitate relative movement of the distal end portion 117 toward the proximal end portion 115, the proximal end portion 115 is held in a stationary position, by for example a pushing member, and the pull/stop wire 127 is pulled to move the distal end portion 117 toward the proximal end portion 115. Alternatively, the proximal end portion 115 can be moved toward the distal end portion 117 by utilizing the pull/stop wire 127 to hold the distal end portion 117 in a stationary position while advancing the proximal end portion 115 toward the distal end portion 117, by for example, advancement of a pushing member associated with the proximal end portion 115.

When in operation, the tissue manipulation element 113 may be located at the distal end portion a pushing member, such as any of the delivery shafts described herein or any other suitable pushing member. Similar to the embodiments discussed above, the guide member can be deployed into a treatment site. The guide member then may be inserted into and through a passageway of the pushing member and through tissue manipulation element 113. With the tissue manipulation element 113 in the deployment configuration, the pushing member may then be used to advance the tissue manipulation element 113 along or over the guide member and into the treatment site. Once in the treatment site, the pull/stop member 127 is utilized to facilitate transforming the tissue manipulation element 113 from the deployment configuration to the deployed configuration. In the deployed configuration, the tissue manipulation element 113 can be rotated about and translated back and forth along the guide member to cut or otherwise disrupt tissue. After a desired amount of tissue has been disrupted, the disrupted tissue can then be collected within the slots 121 between the blade members 119 and in inner cavity 125 defined by the blade members 119. The pull/stop member 127 can be utilized to return the tissue manipulation element 113 to the deployment configuration. As the tissue manipulation element 113 returns to the deployment configuration, the blade members 119 return to their generally linear configuration and the middle sections 123 of each blade member 119 move inwardly, closing down the slots 121 and reducing the size of the inner cavity 125 generally defined by the blade members 119. As the middle sections 123 of the blade members 119 move inwardly, the disrupted tissue becomes trapped within the slots 121 and the inner cavity 125. The tissue manipulation element 113 and pushing member can then be retracted and removed from the treatment site, thereby removing the tissue captured by and within the tissue manipulation element 113. It will be understood that tissue manipulation element 113 may be also used primarily as a tissue removal tool to removal tissue that has been cut or otherwise disrupted by another cutting tool.

Figure 33:
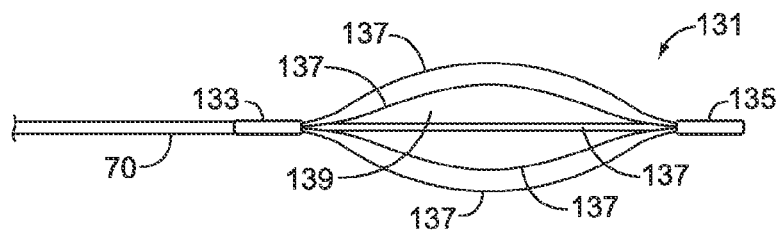
FIG. 33 is a side view of yet another embodiment of a tissue manipulation element constructed in accordance with the present disclosure.

FIG. 33 illustrates another embodiment of a tissue manipulator or manipulation element 131 that can be used as a cutting tool and/or a tissue extraction tool. In this embodiment, the tissue manipulation element 131 includes a proximal end portion 133, a distal end portion 135 and a plurality of blade members 137, extending therebetween. Blade members 137 may be elongated members, such as wires, ribbons or rods, and have tissue manipulation surfaces. The blade members 137 can have a round configuration or a flat configuration. Additionally, the blade members 137 can include sharp surfaces, serrated surfaces or dull or blunted surfaces. The tissue manipulation surfaces of the blade members 137 are spaced or at least partially space in a radial direction from the outer surface of pushing member. The tissue manipulation surfaces also may be radially spaced from the central axis of the tissue manipulation element 131 and/or the central axis of the manipulation element.

Similar to the previously discussed tissue manipulation elements, tissue manipulation element 131 can be located on the distal end of an elongated member or pushing member 70, such as any of the delivery shafts disclosed herein or any other suitable pushing member. For example, the tissue manipulation element 131 can be located on the distal end of a delivery shaft and configured to be translated over a guide member or the tissue manipulation element 131 can be located at the distal end portion of an elongated delivery rod, which does not necessarily require the use of a guide member. When the tissue manipulation element 131 is configured to be advanced along or over a guide member, the proximal end and distal end portions 133 and 135 of the tissue manipulation element 131 may have a generally tubular-like shape with a passageway therethrough. The guide member is inserted through the passageway of the proximal end portion 133, through the inner space 139 generally defined by the blade members 137 and through the passageway of the distal end portion 135 so that the tissue manipulation element 131 may be easily translated or tracked along the guide member.

In one embodiment, tissue manipulation element 131 may be transformable between a first or deployment configuration and a second or deployed configuration. It will be understood, however, that the tissue manipulation element 131 is not necessarily transformable and could just have the single configuration illustrated in FIG. 33. In the deployment configuration, the blade members 137 are extended and generally linear or straight. The deployment configuration allows the tissue manipulation element 131 to easily travel through a deployment cannula or through an endoscopic access site. To transform the tissue manipulation element 131 from the deployment configuration to the deployed configuration, the proximal end and distal end portions 133 and 135 are compressed or moved toward each other. As the proximal end and distal end portions 133 and 135 are move toward each other, the blade members 137 bow or buckle outwardly so that the blade members 137 can effectively contact and cut tissue.

In one embodiment, the tissue manipulation element 131 can be made from a shape memory material that has a natural tendency to form the deployed configuration. Alternatively, the tissue manipulation element 131 could include a pull/stop mechanism similar to the one described above with respect to FIG. 32b.

In operation, the tissue manipulation element 131 can be located at the distal end portion of a pushing member, such as any of the delivery shafts described herein or any other suitable pushing member. Similar to the embodiments discussed above, a guide member is inserted through a cannula and into a treatment site. The guide member is then inserted into and through the pushing member and tissue manipulation element 131, and the pushing member is used to advance the tissue manipulation element along or over the guide member and into the treatment site. Once in the treatment site, the tissue manipulation element 131 is transformed from the deployment configuration to the deployed configuration. In the deployed configuration, the tissue manipulation element 131 can be rotated about and translated longitudinally back and forth along the guide member to cut or otherwise disrupt tissue with the blade members 137. After a desired amount of tissue has been disrupted, the tissue manipulation element 131 can be transformed back into its deployment configuration to capture, trap or ensnare disrupted tissue between the blade members 137 and within the inner space 139 generally defined by the blade members 137. As the tissue manipulation element 131 returns to the deployment configuration, the blade members return to their generally linear, extended configuration, thereby trapping tissue within the inner cavity 139. The tissue manipulation element 131 and delivery shaft can then be retracted and removed from the treatment site, thereby removing the tissue captured by and within the tissue manipulation element 131. It will be understood that tissue manipulation element 131 can be also used primarily as a tissue removal tool to removal tissue that has been cut or otherwise disrupted by another cutting tool.

Figure 34:
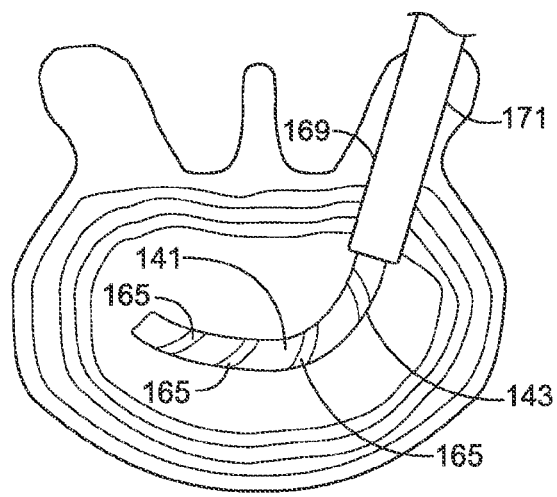
FIG. 34 is a top view of one embodiment of a guide member constructed in accordance with the present disclosure and shown deployed within a disc space.

FIGS. 34-36 illustrate an alternative embodiment of a guide member 141 and an associated tissue manipulation tool 145. Referring to FIG. 34, the guide member 141 is generally similar to the guide members previously discussed herein, except that the surface of the guide member 141 defines a groove or indent 143 that extends along and around the guide member 141 in a generally helical configuration. Similar to the previous embodiments, the guide member 141 can be have any number of various configurations and can be made from a shape memory material that can be pre-set into a desired shape.

Referring to FIG. 35, the tissue manipulation tool 145 includes a pushing member 147, such as the elongated hollow tubular delivery shaft, having a rotatable tissue manipulator or manipulation element 149 located at the distal end portion 151 of the pushing member 147. The pushing member 147 may be any of the delivery shafts described herein or any other suitable pushing member. Similar to the previous embodiments, the pushing member 147 includes a lumen for insertion of the guide member 141 so that the pushing member 147 can be translated along or over the guide member. Preferably, the pushing member 147 has sufficient flexibility to be advanced along the contour of the guide member 141 and sufficient column strength to advance the tissue manipulation element 149 along the guide member 141.

The tissue manipulation element 149 may be any suitable manipulation element, such as a tissue disruption element, for example, a cutting element or scraping element. The tissue manipulation element 149 may also be a tissue removal element. The tissue manipulation element 149 is rotatably coupled to the distal end portion 151 of the pushing member 147 so that the tissue manipulation element 149 rotates independently of and relative to the pushing member 147. In the embodiment shown, the tissue manipulation element 149 is attached to the pushing member 147 by a rotatable coupling 153, which may be any suitable rotatable coupling.

In the illustrated embodiment of the tissue manipulation tool 145, the tissue manipulation element 149 is a tissue cutting element, which includes a proximal end portion 155, a distal end portion 157 and a plurality of blade members 159 extending therebetween. The blade members 159 include tissue manipulation surfaces that are spaced or at least partially spaced in a radial direction from the outer surface of the pushing member and/or from the rotational axis of the tissue manipulation element and/or from the central axis of the tissue manipulation element. The proximal end portion 155 of the tissue manipulation element 149 is rotatably connected to the distal end portion 151 of the pushing member 147 by the rotatable coupling 153. The proximal end and distal end portions 155 and 157 of the tissue manipulation element 149 shown each includes a passageway for insertion of the guide member 141 so that the tissue manipulation element 149 may be translated along the guide member 141. Referring to FIG. 36, the inner wall 161 of the distal end portion 157 that defines the passageway includes a protrusion or projection 163 that engages and rides or follows along the groove 143 of the guide member 141. In will be understood that protrusion 163 that engages the groove 143 does not necessarily have to be associated with the distal end portion 157 of the tissue manipulation element 149, for example, the inner wall of the proximal end portion 155 defining the passageway could include a projection that engages the groove. Alternatively, both the proximal end and distal end portions 155 and 157 may include a projection that engages the groove, or one or more groove engaging projections may be located at any other suitable location along the tissue manipulation tool. As the tissue manipulation element 149 is translated along or over the guide member 141, the protrusion 163 of the inner wall 161 of the distal end portion 157 of the tissue manipulation element 149 rides in or along the helical groove 143 on the guide member 141, which results in rotation or spinning of the tissue manipulation element 149 about the guide member 141. The rate of rotation of the tissue manipulation element 149 can be varied by varying the distance between the coils 165 of the groove 143 extending along and around the guide member 141.

FIGS. 34 and 35 illustrate one exemplary use of the tissue manipulation tool 145 within an intervertebral nuclear space 167. Referring to FIG. 34, the distal end 169 of a delivery cannula 171 is inserted into the nuclear space 167 and the guide member 141 is then deployed through the cannula 171 and into the nuclear space 167. The pushing member 147 is then employed to advance the tissue manipulation element 149 over the guide member 141, through the cannula 171 and into the nuclear space 167. As the tissue manipulation element 149 is advanced over the guide member 141, the protrusion 163 of the distal end portion 157 of the tissue manipulation element 149 follows along groove 143, and the tissue manipulation element 143 rotates about the guide member 141. When the tissue manipulation element 149 is retracted along the guide member 141, the tissue manipulation element 149 rotates in the other direction. As mentioned above, in the embodiment shown, the tissue manipulation element 149 is a cutting element and as the tissue manipulated element 149 is rotated about the guide member 141, blades 159 contact and cut or otherwise disrupt tissue. After the desired amount of tissue have been cut or otherwise disrupted, the tissue manipulation tool 149 is removed.

FIGS. 27-29 illustrate an embodiment of a tissue manipulation tool 160 that can be employed as a scraping tool that is particularly well suited for scraping, cutting or otherwise disrupting endplate tissue, but can also be employed to disrupt nucleus tissue. In several vertebral fusion procedures, a fusion prosthetic implant is implanted into the disc. Bone material, such as bone graft, is then placed adjacent to the implant. The prosthetic maintains the height of the intervertebral disc as the bone graft material promotes bone growth that fuses the endplates of adjacent vertebrae together. It has been discovered that cutting, scraping or otherwise disrupting the surface of the adjacent endplates and causing them to slightly bleed, promotes bone growth and fusion, which can reduce the patient recovery period.

Tissue manipulation tool 160 includes a tissue manipulator or manipulation element 162 and a pushing member 164, which can be any of the elongated shafts described herein. The pushing member 164 includes a proximal end portion (not shown) and a distal end portion 166. Tissue manipulation element 162 is a tissue scraper that has a generally looped blade 168, which is generally similar to a ring-curette. Preferably, the blade 168 is constructed from a flexible, super-elastic material such as nitinol or other similar alloys. The looped blade 168 includes at least one tissue manipulation surface 83 that contacts and disrupts tissue. The tissue manipulation surface is spaced or at least partially spaced in a radial direction from the outer surface of pushing member 164. The tissue manipulation surface also may be radially spaced from the axis of rotation 183 of the tissue manipulation element and/or the central axis of the scrapping tool.

The tissue manipulation tool 160 is capable of being advanced over the guide member through cannula 38 and into the nucleus space. As illustrated in FIG. 27, the tissue manipulation tool 160 can be translated over the distal end portion 34 of the guide member. Once in the nucleus space, the blade 168 of the tissue manipulation element 162 can be orientated so that the top portion of the blade contacts the surface of either one of the endplates of the adjacent vertebrae. When the blade 176 is made from flexible materials, the blade can flex to accommodate a range of disc heights. Once in the desired orientation, the tissue manipulation tool 160 can be cycled back and forth to disrupt the surface of the endplate, causing the surface to bleed. After the surface of one of the endplates has been disrupted, the tissue manipulation tool 160 can be rotated so that the top portion of the blade 168 contacts the surface of the other endplate. The tissue manipulation element 162 can be rotated by applying torque to the proximal end of the pushing member 164. The tissue manipulation tool 160 is again cycled back and forth to disrupt the surface of the endplate. After the surfaces of the adjacent endplates have been disrupted, the tissue manipulation tool 160 is retracted along the guide member and removed from the intervertebral disc.

FIG. 30 illustrates another embodiment of a tissue manipulation tool 170. The manipulation tool 170 includes a tissue manipulation element or section 172 carried on the distal end portion 174 of an elongated member 176, which may be any of the shafts described herein or any other suitable pushing member of sufficient strength to insert and rotate the tissue manipulation element, if desired. The tissue manipulator or manipulation element 172 includes a plurality of tissue engaging brush-like elements, such as tines or bristles 178 for disrupting, disaggregating or capturing tissue. The tissue manipulation element includes tissue manipulation surfaces 81 that contact the tissue for disrupting or capturing tissue. The tissue manipulation surfaces are spaced or at least partially spaced in a radial direction from the outer surface of the pushing member 176. The tissue manipulation surface may also be spaced in a radial direction from the axis of rotation of the tissue manipulation element and/or the central axis of the tissue manipulation element.

Depending on the desired procedure, the tissue manipulation element 172 may be used to disrupt tissue, such as by cutting or scraping, and/or may be used to capture or grab tissue, such as by interassociating, intertangling, or grasping tissue, for extraction of the tissue from the treatment site. For example, the tissue manipulation element 172 of the manipulation tool 170 may be used to disrupt tissue and then capture the disrupted tissue for removal of the tissue from the treatment site. Alternatively, the tissue manipulation tool 170 may be used primarily as a disruption tool wherein a different tool is employed to remove the disrupted tissue from the treatment site, or the tissue manipulation tool 170 may be primarily used as an extractor or extraction tool that is employed to capture and remove residual nuclear and endplate material that has been disrupted by a different disruption tool.

The bristles or tines 178 are preferably made from biocompatible filaments. The tines 178 may vary in strength and flexibility. For example, the tines 178 may be soft, which is more conducive for engaging and capturing nucleus material, or hard, which is more conducive for disrupting nucleus tissue and disrupting and capturing endplate tissue. The tissue manipulation element 172 may also include a combination of soft and rigid tines. The density, placement, length and stiffness of the tines 178 can vary depending on such factors as the particular procedure being performed, the desired result of the procedure, the anatomical characteristics of the treatment site, the amount and type of tissue to be disrupted and/or extracted and the location of treatment site. For example, by configuring the tines 178 of the tissue manipulation element 172 to be dense, stiff and/or sharp, the tissue manipulation element 172 may be used to disrupt nuclear and endplate material. The tines 178 of the tissue manipulation element 172 may also be configured to engage and extract disrupted tissue from the treatment site. Additionally, the tines 178 may be in virtually any configuration. For example, the tines 178 may be in parallel rows and/or columns, they may be in a uniform spiral arrangement or they may be randomly spaced apart. Furthermore, the tines may be of a uniform size and shape or may vary in size and shape.

In use, the tissue manipulation tool 170 is mounted onto and advanced over the guide member, through the cannula 38 and into the nucleus space 26 of vertebra 24. As the tissue manipulation element 172 is advanced over the distal end portion 34 of the guide member 30, it follows along the pre-defined path of the guide member 30. As the tissue manipulation tool 170 is translated back and forth along the guide member 30 and, optionally, rotated about the guide member 30 (as generally indicated by arrows 180 and 182) the tissue manipulation element 172 disrupts and captures tissue for removal. The tissue manipulation tool 170, with tissue attached thereto, is then retracted and removed from the intervertebral disc 24. The tissue manipulation tool 170, now outside of the patient may be cleaned and then reinserted into the patient to disrupt and capture more material. Alternatively, a new unused tissue manipulation tool can be inserted over the guide member 30 and into the nucleus space 26. The same procedure is repeated until lack of tissue on the tissue manipulation element indicates that the nucleus space 26 has been cleared of the desired amount of tissue.

Figure 43:
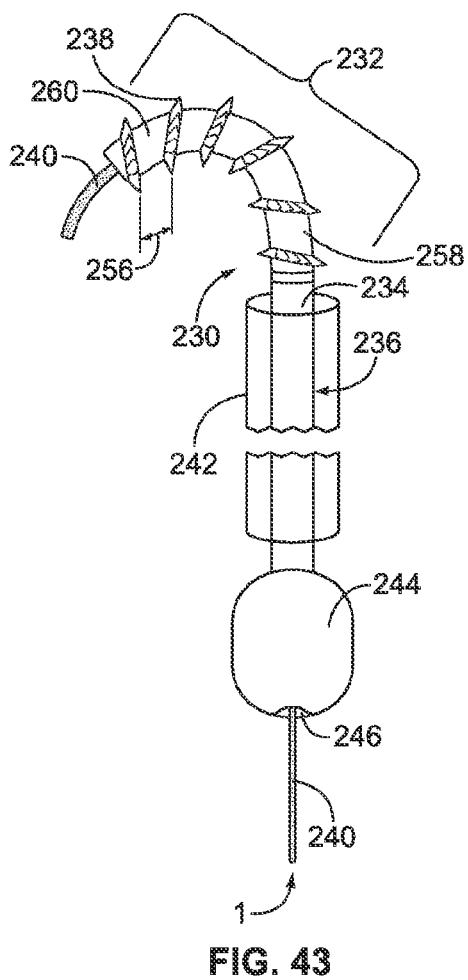
FIG. 43 is a side view of one embodiment of a tissue manipulation tool constructed in accordance with the present disclosure.

FIGS. 43-52 illustrate another embodiment of a tissue manipulation tool 230 and a method of manufacturing such a tool. Referring to FIG. 43, similar to the manipulation tool 170, tissue manipulation tool 230 includes a tissue manipulation element or section 232 located at the distal end portion 234 of a pushing or elongated member 236, which may be any of the shafts described herein or any other suitable pushing member. The tissue manipulation element 232 includes a plurality of radiating brush-like elements, such as tines or bristles 238. Preferably, the tines 238 radiate from the tissue manipulation element 232 in a generally helical pattern. The tines 238 may be used to disrupt and/or extract tissue. The tissue manipulation element 232 may be flexible so that it is advanceable along a guide member 240 through a cannula 242 and into a treatment site. Preferably, the tissue manipulation element 232 is sufficiently flexible so that it may be inserted through a single access port and substantially reach all of the desired locations within the treatment site. Alternatively, the tissue manipulation element 232 may also be substantially rigid. Preferably, the components of the tissue manipulation tool 230 are made from radiopaque materials that are visible under fluoroscopy, or other imaging system, during advancement of the tool into the patient.

The manipulation tool 230 may also include a handle 244 that may be used to translate the manipulation tool 230 along the guide member 240 and rotate the manipulation tool 230 about the guide member 240. The handle 244 and the pushing member 236 may be of unitary construction or the handle 244 and pushing member 236 may be separate pieces that are attached to each other by, for example, adhesive bonding, welding or the like. The handle 244 is preferably generally ball shaped for easy gripping and has a passageway therethrough for the passage of the guide member 240.

The overall outer diameter of the tissue manipulation element 232 can vary in size depending on the particular application. For disrupting and/or removing tissue from an intervertebral disc, the outer diameter may be between about 0.16 inches (4 mm) and about 0.47 inches (12 mm). In one embodiment, the outer diameter is about 0.24 inches (6 mm). The length of the tissue manipulation element 232 may also vary depending on the particular application. For example, the length of the tissue manipulation element may be between about 0.20 inches (5 mm) and about 1.4 inches (35 mm). In one embodiment, the length is about 0.6 inches (15 mm).

Figure 48:
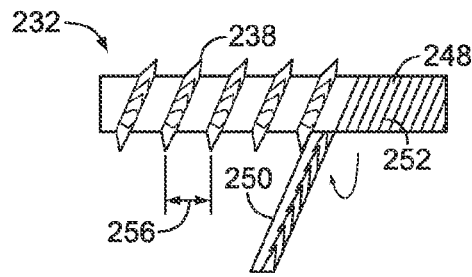
FIG. 48 is a perspective view of an internal support member shown with an elongated member being mounted to the internal support member.

Referring to FIG. 48, the tissue manipulation element 232 includes an internal support member 248 and at least one elongated member 250 mounted over the internal support member. The elongated member 250 includes a plurality of tines 238, which provides the brush-like appearance of the tissue manipulation element. The internal support member 248 is preferably a flexible tubular member, such as a spring coil, a hollow braided tube, laser-cut hypotube or the like. The internal support member 248 may be made from materials such as metal, metal alloys or a polymer. Preferably, the internal support member 248 is made from stainless steel, nitinol or titanium. Additionally, the material of the internal support member 248 may be radiopaque or a radiopaque impregnated material so that it is visible under fluoroscopy.

Figures 44, 45:
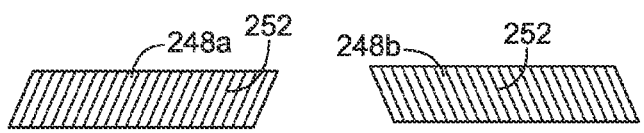
FIG. 44 is a side elevation view of one embodiment of an internal support member.
FIG. 45 is a side elevation view of another embodiment of an internal support member.

Referring to FIG. 44, the internal support member 248 preferably includes an outer surface 252 to which the elongated member 250 may be mounted. In one embodiment, the elongated member 250 is wound, preferably helically, around the outer surface 252 of the internal support member 248, as shown in FIG. 48. As explained in more detail below, the elongated member 250 may be attached and/or bonded to the internal support member 248.

Preferably, the inner surface (not shown) of the internal support member 248, which defines a passageway for receiving the guide member therethrough, is a smooth, flexible surface that assists in articulating the tissue manipulation element 232 over the guide member. The internal support member 248 preferably has an inner diameter that is slightly larger than the outer diameter of the guide member 240. For example, if the guide member 240 has an outer diameter of about 0.060 inch (1.5 mm), the inner diameter of the internal support member may be about 0.080 inch (2.0 mm). The outer diameter of the internal support member 248 may be between about 0.09 inch (2.25 mm) and about 0.2 inch (4.0 mm). However, the inner diameter of the internal support member 248 may be larger or smaller depending on the particular application. Preferably, the inner diameter is sufficiently large to accommodate the bending of the tissue manipulation element 232 along the guide member 240.

The internal support member 248 also provides a mechanical support that aids in preventing the helically wound elongated member(s) of the tissue manipulation element 232 from collapsing and/or binding onto guide member 240 as the tissue manipulation element 232 is articulated over the guide member 240 and/or rotational or tensile forces are applied to the tissue manipulation element 232. The internal support member 248 and the pushing member 236 may be of a single unitary construction or the internal support member 248 may be attached to the pushing member 236, by for example welding or adhesive bonding.

FIGS. 44 and 45 illustrate two embodiments of the internal support member 248a and 248b. In each of these embodiments, the internal support members 248a and 248b are formed from a wire or a ribbon, such as a stainless steel wire or flat ribbon, that has been wound into a generally helical coil. When a ribbon is utilized to form the coiled internal support member, the ribbon may provide a greater surface area onto which the elongated member may be attached. When a wire is utilized to form the coiled internal support member, the outer diameter of the wire is preferably between about 0.09 inch (2.25 mm) and about 0.2 inch (4.0 mm), other sizes may also be suitable. The wire or ribbon may be wound into a right-handed coiled internal support member 248a (FIG. 44) or a left-handed coiled internal support member 248b (FIG. 45).

Additionally, the internal support member may be a single coil structure or a multi-layer coiled structure. FIG. 56 illustrates one example of a counter-wound dual layer coil internal support member 248c. The internal support member 248c includes an outer coil 247 and an inner coil 249. The outer coil 247 and inner coil 249 are preferably wound in opposite directions. In the illustrated embodiment, the outer coil 247 is wound in a right-hand fashion and the inner coil is wound in a left-hand fashion. Dual layer coiled internal support members with opposite wound inner and outer coils can provide greater torsional stiffness and enhanced response of torque transmission along the tissue manipulation element in either a clockwise or counter-clockwise rotation, which may be particularly helpful in procedures that require disruption and removal of tougher and stronger tissue. For example, a dual layered counter-wound coiled internal support member can enhance one to one torque transmission along the tissue manipulation element 232. In other words, the dual layered counter-wound configuration can enhance the transfer of torque from the proximal end of the internal support member to the distal end of the internal support member.

FIGS. 60 and 61 illustrate alternative embodiments of the internal support member. In these embodiments, the internal support members 248d and 248e are braided hollow tubular members. The internal support members 248d and 248e may be multi-layer extruded tubular members that are reinforced with metal wire or ribbons to provide flexible, torqueable tubular members. The internal support members 248d and 248e may have a smooth inner wall that defines a passageway for receiving the guide member and provides smooth articulation over the guide member. The outer surface of each of the internal support members 248d and 248e may provide a support to which the elongated member can be mounted. The characteristics of the braided tubular members may be optimized for a particular application by varying the braid wire material and geometry, the braid pattern, and the polymer extrusion materials and thickness.

FIGS. 57-59 illustrate other alternative embodiments of the internal support member. In these embodiments, the internal support members 248f, 248g and 248i are flexible hypotubes made from a metal, such as stainless steel or nitinol, or any other suitable material. In FIG. 57, the internal support member 248f has a simple spiral cut pattern 251. In FIGS. 58 and 59, the internal support members 248g and 248i have more complex cut patterns 253 and 255. The cut patterns provide the internal support members 248f, 248g and 248i with sufficient flexibility to be translated over the guide member. The cut pattern may be cut in a manner that permits the transmission of torque through the hypotube in either a clockwise direction or counter clockwise direction. Preferably, the cut pattern permits transmission of torque in both directions. The hypotubes can be optimized for a particular application by varying the material, thickness and geometry of the hypotube and the cut patterns.

When the internal support member is constructed from a hypotube, the hypotube may provide both the pushing member and the internal support member of the tissue manipulation element. In such an embodiment, the distal end portion of the hypotube forms the internal support member and the proximal end portion forms the pushing member. The distal end portion has a cut pattern that makes the distal end portion suitable for use as the internal support member. The proximal end portion may be solid without any cut patterns or includes the same or a different cut pattern than the distal end portion.

Turning now to the elongated member 250 that is mounted onto the internal member 248. The elongated member 250 may be an elongated ribbon, wire or strip of material that, preferably, has a larger length than its width. Additionally, when the elongated member 250 is a ribbon or a strip of material, the thickness of the elongated member may be thin and, preferably, significantly less than the elongated member's width. The elongated member 250 is preferably made of materials that are biocompatible and suitable for at least temporary exposure within the body. The materials also are preferably capable of withstanding forces associated with tissue disruption and extraction. Such materials may include metals, metal alloys, polymers or any other suitable material or combination of materials. For example, the materials of the elongated member may include stainless steel, nitinol, titanium, PEEK, polyethylene or nylons. Preferably, the material is radiopaque so that it is visible under fluoroscopy. When the elongated member 250 is made from a polymer, its visibility under fluoroscopy may be enhanced by impregnating it with barium sulfate or including radiopaque markers, at least at the proximal and distal ends of the elongated member.

Figure 46:
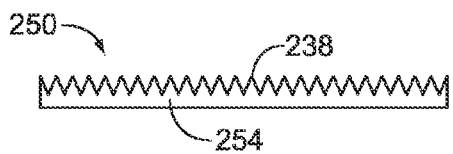
FIG. 46 is a top view of one embodiment of an elongated member.

Referring to FIG. 46, the elongated member 250 includes a main body 254 and a plurality of projections, such as tines 238, extending from one or both of the edges of the main body 254. The tines 238 extend at an angle from the plane of the main body 254. The tines 238 and the main body 254 may be of a single unitary construction or they may be separate pieces that are assembly together. For example, the main body 254 may be a polymer material to which metal tines 238 are attached during the manufacturing process. Alternatively, the main body 254 may be a metal material to which polymer tines 238 are attached. In another embodiment, wherein the tines 238 and the main body 254 are of a unitary construction, the tines 238 and main body 254 may be formed from a strip of material by stamping, punching or cutting out portions of the material along one or both edges of the material. The elongated member's main body 254 and tines 238 may also be formed by lithography or molding.

The tines 238 can have virtually any shape, such as triangular, rectangular, sawtooth, trapezoidal or other desired shape. The tines 238 may also be beveled or serrated. Some of non-limiting exemplary shapes of the tines 238 are illustrated in FIG. 52. Additionally, the plurality of tines 238 along the length of an elongated member 250 may be uniform in size and shape, or the shape and size of the tines 238 may vary along the length of the elongated member 250. Also, the tines 238 and the main body 254 may include features that reduce stress that is applied to the elongated member 250 during tissue disruption and/or extraction. Such stress reduction features may include stress-relieved corners and fillets at the junction between the tine 238 and the main body 254 of the elongated member 250.

Figure 47:
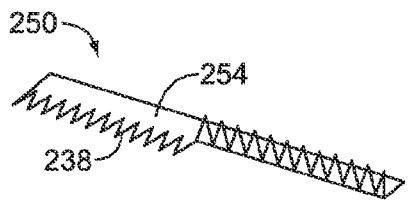
FIG. 47 is a perspective view of the elongated member of FIG. 46 shown with several tines in a bent configuration.
Figures 50, 51:
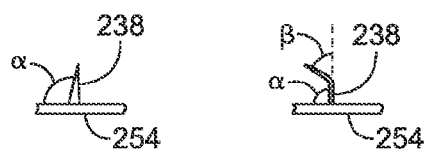
FIG. 50 is a side view of a main body and tine of an elongated member shown with the tine bent out of the plane of the main body.
FIG. 51 is a side view of a main body and tine of an elongated member shown with a tine bend at two locations.

FIGS. 46 and 47 illustrate one embodiment of a method of forming the elongated member 250. FIG. 46 illustrates an elongated member 250 in which the tines 238 are initially in the same plane as the main body 254. Such a structure may be constructed, for example, by stamping, punching or cutting out portions along the edges of a strip of material to form a main body 254 and a plurality of tines 238. As illustrated in FIGS. 47 and 50, the tines 238 are then bent or otherwise deformed so that the tines 238 extend at an angle from the plane of the main body 254. The plurality of tines 238 may all be bent at the same angle, or the tines 238 may be bent at varying angles. Referring to FIG. 51, optionally, the tines 238 also may be compoundedly bent at two or more angles. The shape, size, angle of extension, bend angle and material of the tines may be varied to optimize the tines for cutting and/or capturing a particular type or types of tissue.

After the elongated member 250 has been formed, it is mounted to the internal support member 248. Turning to FIG. 46, in one embodiment, the elongated member 250 is wound or wrapped around the internal support member 248 in a helical fashion. When a coiled internal support member is utilized, the elongated member may be counter-wound with respect to the coiled internal support member. The counter winding of the elongated member increases structural integrity of the tissue manipulation element and may prevent undesired mechanical interactions. For example, the counter winding can prevent stretching or enlargement of the tissue manipulation element when exposed to rotational forces. The elongated member 250 is wound so that the tines 238 project radially outward from the internal support member 248 so as to form a brush-like structure. Preferably, the elongated member 250 is tightly wound around the internal support member 248. The pitch of the winding may be open or closed and the pitch may vary along the length of the internal support member 248 as necessary to provide more or less flexibility along the length of the tissue manipulation element being formed. The distance or pitch between each winding of tines 238 (designated as 256 in FIGS. 43 and 48) of the tissue manipulation element 232 may be controlled by the pitch of the helically wound elongated member 250 and the width of the elongated member 250.

To help ensure that the elongated member 250 does not unwind or detach from the internal support member 248, the elongated member 250 may be coupled to the internal support member 248 by a mechanical coupling or otherwise. Attachment of the elongated member to the internal support member also helps the elongated member from expanding, stretching and/or buckling when the tissue manipulation element is exposed to torsional or axial forces. For example, the elongate member 250 may be secured to the internal support member 248 by a bonding agent, soldering, laser welding, RF welding or the like. Alternatively or additionally, an additional attachment element may be used to secure the elongated member 250 to the internal support member 248. For example, a wire member may be coiled around the elongated member 250 and between the tines 238 to secure the elongated member 250 to the internal support member 248. In yet another alternative, coupling may be achieved by plastic deformation of the elongated member 250. For example, the elongated member 250 may be wound onto the internal support member 248 under tension so that the elongated member 248 takes a substantially identical shape as the internal support member 248, much like when a wire coil is wound under tension on a mandrel. In yet a further coupling alternative, when the elongated member 250 is made from a shape memory metal and a polymer, an appropriate heating protocol may be used to substantially conform the shape of the wound elongated member 250 to shape of the internal support member 248.

The proximal end portion 258 and the distal end portion 260 of the tissue manipulation element 232 may encounter different forces and stresses during use. Thus, the proximal end portion 258 and the distal end portion 260 may be coupled to the internal support member 248 in different manners. For example, the shear forces encountered between the proximal end portions of the internal support member and the elongated member may be higher than the shearing forces between the distal end portions of the two. Thus, the elongated member's proximal end portion and distal end portion each may be coupled to the internal support member in a manner that is particularly well suited for withstanding the unique forces and stresses that each end portion may encounter.

Figure 49:
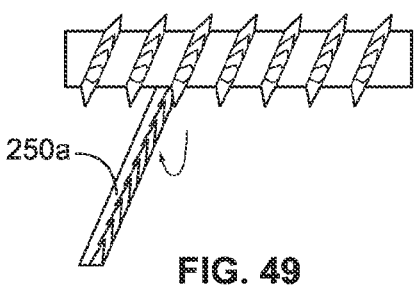
FIG. 49 is a perspective view of an internal support member shown with a second or subsequent elongated member being mounted to the internal support member.

The tissue manipulation element 232 may include a single elongated member or a plurality of elongated members mounted onto the internal support member 248. Referring to FIG. 49, a second elongated member 250a may be wound around the internal support member 248. The second and other subsequent elongated members 250a may be wound so that it overlaps the immediate preceding elongated member 250 or it may be wound so that it is located in between the windings of the preceding elongated member 250 or a combination of both. The second and other subsequent elongated members 250a may be used to increase the density of the tines 238 of the tissue manipulation element 232, vary the height of the tines 238 or vary the angle and direction of the tines 238. Thus, the second and subsequent elongated members 250a may include tines 238 that have shapes and sizes that are different from those of the previous mounted elongated member(s) 250 and/or tines that extend at a different angle and/or direction than those of the previous elongated member(s) 250.

FIGS. 53-55 illustrate some exemplary embodiments of tissue manipulation elements 232a, 232b and 232c having tines 238 of different configurations. All of the embodiment shown in these figures may be tissue manipulation elements that include a single elongated member or multiple elongated members. FIG. 53 shows a tissue manipulation element 232a in which all of the tines 236a have a substantially uniform height. FIG. 54 illustrates a tissue manipulation element 232b in which the height of the tines 238b located nearer the distal end portion 260b of the tissue manipulation element 232b are larger than the height of the tines 238b located nearer the proximal end portion 262b. FIG. 55 illustrates a tissue manipulation element 232c in which the height of the tines 238c located nearer the proximal end portion 262c of the tissue manipulation element 232c are larger then the height of the tines 238c nearer the distal end portion 260c. Varying the height along the length of the tissue manipulation member may be useful for penetrating and treating wedge shaped treatment sites. For example, a tissue manipulation element that has tines which are smaller at the proximal end portion and larger at the distal end portion may be effective in treating a lordodic disc space. The varying height of the tines 238 may be accomplished by varying the height of the tines along an individual elongated member 250 or by varying the height of the tines between elongated members.

FIG. 37 illustrates another embodiment of a tissue manipulation tool. The tissue manipulation tool may include a pushing member 171, such as a rod, ribbon or wire, that has a tissue manipulator or manipulation element 173 located at the distal end of the elongated member. In the embodiment shown, the tissue manipulation element 173 includes tines 175. The tissue manipulation element 173 may be substantially similar to the tissue manipulation elements 172 and 232 described above. The elongated member 171 may be constructed of a shape memory material that is pre-set to a desired shape. When constructed from a shape memory material, the elongated member 171 may be straightened for deployment through a cannula 177 and then returned to its pre-set shape upon exiting the cannula. In one embodiment, the elongated element 171 may be a twisted wire, such as a twisted nitinol wire.

Figure 38:
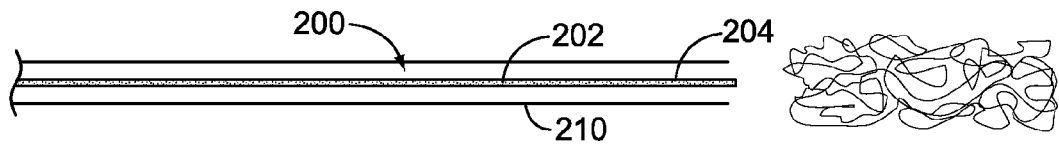
FIG. 38 is a side view of another embodiment of a tissue manipulation tool constructed in accordance with present disclosure.
Figure 39:
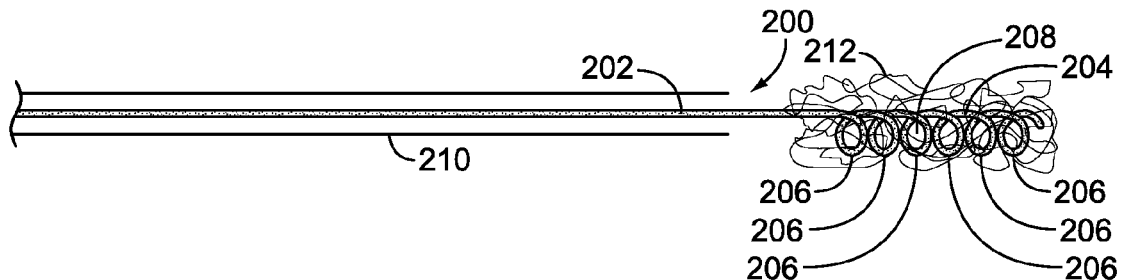
FIG. 39 is a side view of the tissue manipulation tool of FIG. 38 shown in the deployed configuration.
Figure 40:
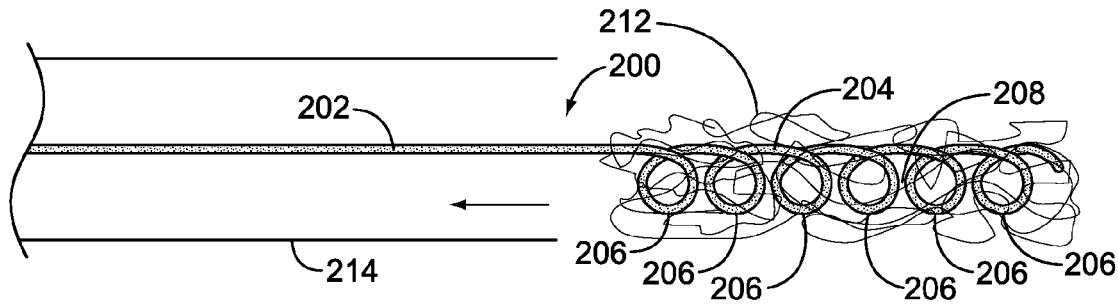
FIG. 40 is a side view of the tissue manipulation tool of FIG. 38 shown being retracted into a cannula.

FIGS. 38-40 illustrate another embodiment of a tissue manipulation tool that may be used as a tissue extraction tool. Referring to FIG. 39, the tissue extraction tool 200 includes an elongated element 202 having a generally helically shaped distal end portion 204. The generally helically shaped distal end portion 204 includes a plurality of coils 206. The coils 206 generally define an inner space or volume 208. Preferably, at least the helically shaped distal end portion 204 of the elongated element 202 is made from a shape memory material, for example nitinol, so that at least the distal end portion 204 of the elongated element 202 can be transformed or constrained into a generally linear or straight configuration for deployment through a delivery cannula 210, as shown in FIG. 38. Referring back to FIG. 39, as the distal end portion 204 of the tissue extraction tool 200 exits the distal end of the cannula 210, it transitions into its helical shape and travels through the tissue 212 to be removed. The distal end portion 204 may be inserted into the tissue 212 in a linear or rotational translation. The tissue 212 becomes ensnared, entangled or otherwise entrapped in the inner space 208 generally defined by the coils 206. It will be understood that the extraction tool 200 does not necessarily need to be straightened for insertion into the tissue and that the extraction tool can be inserted into tissue in its helical configuration.

Turning to FIG. 40, after the helically shaped distal end portion 204 is in the desired position, the delivery cannula 210 may be removed and a second larger cannula 214 may be placed over the extraction tool 200. Preferably, the size of the inner diameter of the internal lumen of the second cannula 214 is about the same size or slightly larger than the outer diameter defined by the coils 206 of the helical distal end portion 204 of the extraction tool 200. After the second cannula 214 is in the desired location, the tissue extraction tool 200 is retracted into the second larger cannula 214. As the tissue extraction tool 200 is retracted, the pitch of each coil 206 slightly tightens, reducing the inner space 208 generally defined by the coils 208, thereby trapping the tissue in the inner space 208 and between the coils 206. The extraction tool 200 with the tissue 212 trapped within the coils 206 is then retracted into the second delivery cannula 214 to remove the tissue 212 from the treatment site.

If desired, a secondary element may be utilized to assist facilitating the tightening of the coils 206 and the collapse of the inner space 208. For example, the secondary element may be an elongated stop mechanism that tracks or slides along the extraction tool 200 and contacts one or more the distal most coils or the distal tip of the extraction tool 200. The stop mechanism may contact the distal most coils and act as a stop that maintains the distal most coils in a stationary position. With the distal most coils held in a stationary position, the extraction tool 206 is retracted, causing the coils 206 to tighten, which reduces the inner space 208 generally defined each coil.

In alternative embodiment, the extraction tool 200 can be guided by a guide member into the tissue. A guide member, which may be any of the guide members discussed above, is inserted into the tissue. The distal end portion 204 of the extraction tool 200 may then be slideably attached to the guide member so that the extraction tool 200 can be advanced or tracked along the guide member. For example, the distal end portion 204 of the extraction tool 200 may include an attachment member, such as a collet or tube or ringlet into which the guide member can be inserted.

Figure 41:
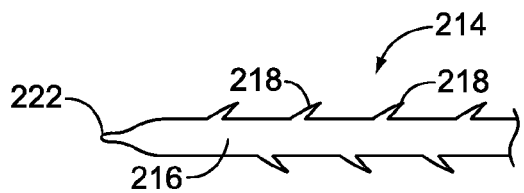
FIG. 41 is a side view of yet another embodiment of a tissue manipulation tool constructed in accordance with the present disclosure.
Figure 42:
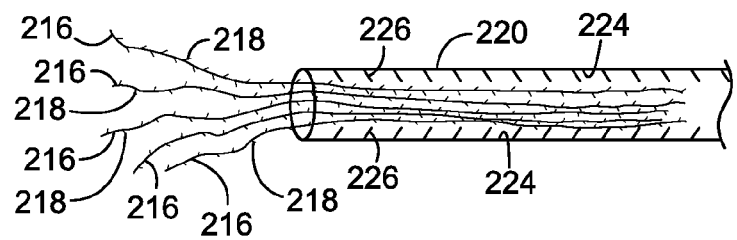
FIG. 42 is a side view of the tissue extraction tool of FIG. 41 and one embodiment of a deployment cannula.

FIGS. 41 and 42 illustrate yet another embodiment of an extraction tool 214. Referring to FIG. 40, the extraction tool 214 can include an elongated member 216 that has a plurality of projections, such as barbs 218, extending radially outwardly from the elongated member 216. The elongated member 216 can be, for example, a rod, wire, or ribbon. Preferably the elongated member 216 is made from a biocompatible material. The elongated member may be made from a metal, such as stainless steel, or a metal alloy, such nitinol, or a biocompatible polymer. The barbs 218 may extend from the elongated member 216 in virtually any pattern, for example, spiral, columns and rows or randomly. Preferably, the barbs 218 are "one way" barbs that extend at an angle relative to the elongated member 216 and in a generally proximal direction. Additionally, the barbs 218 may have any variety of configurations, including for example, sharp, blunt, straight, hook shaped, zig-zagged, etc.

Turning to FIG. 42, when in use, one or more elongated members 216 are inserted into the tissue to be removed through a cannula 220. Preferably, the angle and direction of extension of the barbs 218 are such that the elongated members 216 travel through the tissue relatively easily. In the embodiment shown, the barbs 218 are "one way" barbs that extend in a proximal direction, which is also in a direction that is opposite the direction of insertion of the elongated member into the tissue. Because of the direction of the barb's extension, the elongated members 216 and barbs 218 may be inserted into the tissue with minimal resistance. Additionally, as shown in FIG. 41, the distal tip 222 of the elongated member 216 may be pointed to penetrate through tissue. Also, rigidity of the distal tip 222 may be configured so that the tip is suitable for penetration into one type of tissue but unable to penetrate through a second type of tissue. For example, the distal tip 222 may be configured to penetrate through nucleus tissue, but not through annulus tissue.

After the elongated members 216 have been inserted into the tissue a desired amount, the elongated members 216 are retracted back into the cannula 220. As the elongated members 216 are being retracted, the "one way" barbs 218 contact the tissue and entangle, ensnare, hook or otherwise capture the tissue. The elongated members 216, with the tissue captured by the barbs 218, continue to be retracted into the cannula 220 to remove tissue from the treatment site.

After the elongated members 216 have been retracted into the cannula 220, the elongated members 216 may be removed from the cannula 220 and a new, unused set of elongated members can be inserted through the cannula 220 into the treatment site to retrieve further tissue. Alternatively, the cannula 220 can include a barb cleaning mechanism. In the illustrated embodiment, the inner wall 224 of the deployment cannula 220 includes a plurality of cleaning projections, such as barbs 226. The cleaning barbs 226 may also be "one way" barbs that extend from the inner wall 224 at an angle and in the same direction as the barbs 218 of the elongated members 216. The cleaning barbs 226 may also extend in any other suitable direction, such as generally perpendicular to the inner wall of the cannula, and may have any configuration. Because the cleaning barbs 226 extend in the same direction as the barbs 218 of the elongated members 216, the elongated members 216, having tissue attached to the barbs 218, are retractable into the cannula 220 with minimal resistance.

After the elongated members 216 have been retracted into the cannula 220, the elongated members 216 are then again advanced out of the cannula 220. As the elongated members 216 are advanced out of the cannula 220, the cleaning barbs 226 contact the tissue associated with the barbs 218 of the elongated members 216 and strip, clean or otherwise remove the tissue from the barbs 218 of the elongated members 216. Thus, the cleaned elongated members 216 are inserted back into the treatment site to capture and remove additional tissue. The elongated members 216 can be repeatedly advanced out of and retracted into the cannula 220 to continually remove tissue from the treatment site.

The cutting, scraping and extraction tools described herein can be used in conjunction with each other to perform discectomy procedures. Alternatively, each tool can be used separately in any procedure for its individual purpose. Additionally, when used in conjunction with one another, the tools can be deployed over the same guide member, or different guide members, each having a different configuration, can be used to deploy each of the tools.

Additionally, the discectomy tools described herein can be supplied in a kit. The kit can include one or more tissue manipulation tools, such as the above-described cutting tools, scraping tools and tissue extraction tools. The kit can also include one or more guide members. Optionally, the kit can also include a working cannula for deploying the guide member and discectomy tools. In one embodiment, the kit can include a sterilized package or tray containing one of more guide members and one of more the above mentioned manipulation tools as well as other elements that can be used in combination with the discectomy tools.

Although the present invention is described in light of the illustrated embodiments, it is understood that this for the purposes illustration and not limitation. Other applications, modifications or use of the support or distraction device may be made without departing for the scope of this invention, as set forth in the claims now or hereafter filed.

What is claimed is:

1. An intervertebral disc preparation system for preparing an intervertebral disc space for implantation of a prosthetic device, comprising:
    a guide member having a proximal end portion and a distal end portion, the distal end portion of the guide member changeable from a generally linear deployment configuration for insertion into the intervertebral disc space to a predefined less linear deployed configuration within the intervertebral disc space;
    at least one elongated member having a distal end portion and an outer surface, the elongated member adapted to be moveable longitudinally along the guide member; and
    at least one tissue manipulator for manipulating tissue within the intervertebral disc space, the tissue manipulator being one or more of a tissue cutter for cutting tissue, a tissue scraper for scraping tissue and a tissue extractor for removing tissue from the intervertebral disc space, the tissue manipulator being located at the distal end portion of the elongated member and having at least one tissue manipulation surface that is spaced in a radial direction from the outer surface of the elongated member.

2. The system of claim 1 in which the tissue manipulator is rotatable about the guide member.

3. The system of claim 1 in which the deployed configuration of the guide member is arcuate.

4. The system of claim 1 in which the deployed configuration of the guide member is a spiral configuration.

5. The system of claim 1 in which the tissue cutter comprises at least one blade member.

6. The system of claim 5 in which the at least one blade member comprises a plurality of blade members.

7. The system of claim 1 in which the tissue manipulator is changeable between a deployment configuration for insertion into the intervertebral disc space and a deployed configuration within the intervertebral disc space.

8. The system of claim 1 in which the elongated member and/or tissue manipulation element are constructed from a radiopaque material.

9. An intervertebral disc preparation system for preparing an intervertebral disc space for implantation of a prosthetic device, comprising:
    a guide member having a proximal end portion and a distal end portion, the distal end portion of the guide member changeable from a generally linear deployment configuration for insertion into the intervertebral disc space to a predefined less linear deployed configuration within the intervertebral disc space;
    at least one elongated member having a distal end portion and an outer surface, the elongated member adapted to be moveable longitudinally along the guide member; and
    at least one tissue manipulator for manipulating tissue within the intervertebral disc space, the tissue manipulator comprising a tissue scraper configured for scraping a vertebral endplate adjacent the intervertebral disc space, the tissue scraper being located at the distal end portion of the elongated member and having at least one surface for contacting and scraping tissue wherein the surface is spaced in a radial direction from the outer surface of the elongated member.

10. The system of claim 9 in which the tissue manipulator is rotatable about the guide member.

11. The system of claim 9 in which the deployed configuration of the guide member is arcuate.

12. The system of claim 9 in which the deployed configuration of the guide member is a spiral configuration.

13. The system of claim 9 in which the tissue scraper comprises a blade wherein the blade includes the surface for contacting and scraping tissue.

14. The system of claim 13 in which the blade is in a looped configuration.

15. The system of claim 9 in which the at least one tissue manipulator further includes a second tissue manipulator comprising a tissue extractor for removing tissue from the intervertebral space.

16. The system of claim 15 in which the at least one elongated member includes a second elongated member and the tissue extractor is located on the second elongated member.

17. The system of claim 15 wherein the tissue extractor includes a plurality of radially extending projections adapted to capture tissue.

18. An intervertebral disc preparation system for preparing an intervertebral disc space for implantation of a prosthetic device, comprising:
    a guide member having a proximal end portion and a distal end portion, the distal end portion of the guide member changeable from a generally linear deployment configuration for insertion into the intervertebral disc space to a predefined less linear deployed configuration within the intervertebral disc space;
    at least one elongated member having a distal end portion and an outer surface, the elongated member adapted to be moveable longitudinally along the guide member; and
    at least one tissue manipulator for manipulating tissue within the intervertebral disc space, the tissue manipulator comprising a tissue extractor for removing tissue from the intervertebral space, the tissue extractor being located at the distal end portion of the elongated member and having a plurality of radially extending projections adapted to capture tissue wherein the radially extending projections include tissue manipulation surfaces spaced in a radial direction from the outer surface of the elongated member.

19. The system of claim 18 in which the tissue manipulator is rotatable about the guide member.

20. The system of claim 18 in which the deployed configuration of the guide member is arcuate.

21. The system of claim 18 in which the deployed configuration of the guide member is a spiral configuration.

22. The system of claim 18 in which the radially extending projections include a plurality of tines or bristles.

23. The system of claim 18 in which the radially extending projections are in a generally helical pattern.

* * * * *